(12) United States Patent
Han et al.

(10) Patent No.: US 10,723,818 B2
(45) Date of Patent: Jul. 28, 2020

(54) COMPOUND AND TRANSITION METAL COMPOUND

(71) Applicant: LG Chem, Ltd., Seoul (KR)

(72) Inventors: Hyo Jung Han, Daejeon (KR); Eun Jung Lee, Daejeon (KR); Choong Hoon Lee, Daejeon (KR); In Sung Park, Daejeon (KR); Seul Ki Kim, Daejeon (KR); Young Hoon Na, Daejeon (KR); Ik Je Choe, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 16/698,047

(22) Filed: Nov. 27, 2019

(65) Prior Publication Data

US 2020/0095347 A1 Mar. 26, 2020

Related U.S. Application Data

(62) Division of application No. 15/749,309, filed as application No. PCT/KR2017/001503 on Feb. 10, 2017, now Pat. No. 10,538,603.

(30) Foreign Application Priority Data

Feb. 12, 2016 (KR) .................. 10-2016-0016517
Feb. 9, 2017 (KR) .................. 10-2017-0018307

(51) Int. Cl.
| | | |
|---|---|---|
| C08F 4/00 | (2006.01) |
| C08F 4/64 | (2006.01) |
| C07F 7/28 | (2006.01) |
| C07D 401/04 | (2006.01) |
| B01J 31/16 | (2006.01) |
| C07F 7/00 | (2006.01) |
| B01J 31/18 | (2006.01) |
| C08F 210/02 | (2006.01) |
| C08F 210/06 | (2006.01) |
| C08F 210/16 | (2006.01) |

(52) U.S. Cl.
CPC .......... *C08F 4/64089* (2013.01); *B01J 31/16* (2013.01); *B01J 31/184* (2013.01); *C07D 401/04* (2013.01); *C07F 7/00* (2013.01); *C07F 7/28* (2013.01); *C08F 4/64148* (2013.01); *C08F 210/02* (2013.01); *C08F 210/06* (2013.01); *C08F 210/16* (2013.01); *B01J 2231/12* (2013.01); *B01J 2531/004* (2013.01); *B01J 2531/0266* (2013.01); *B01J 2531/48* (2013.01); *B01J 2531/49* (2013.01)

(58) Field of Classification Search
None
See application file for complete search history.

(56) References Cited

U.S. PATENT DOCUMENTS

| | | |
|---|---|---|
| 5,064,802 A | 11/1991 | Stevens et al. |
| 9,481,747 B2 | 11/2016 | Park et al. |
| 2004/0097670 A1 | 5/2004 | Nagy et al. |
| 2005/0014915 A1 | 1/2005 | Liu |
| 2010/0234601 A1 | 9/2010 | Halland et al. |
| 2016/0046735 A1 | 2/2016 | Lee et al. |

FOREIGN PATENT DOCUMENTS

| | | |
|---|---|---|
| EP | 2873671 A1 | 5/2015 |
| KR | 1999007920 | 1/1999 |
| KR | 20060058679 A | 5/2006 |
| KR | 2008-0101542 A | 11/2008 |
| KR | 2010-0024963 A | 3/2010 |
| KR | 2013-0089490 A | 8/2013 |
| KR | 101528102 B1 | 6/2015 |

OTHER PUBLICATIONS

International Search Report From PCT/KR2017/001503 dated May 19, 2017.
Extended European Search Report including Written Opinion for Application No. EP17750475.0 dated Sep. 20, 2018.

*Primary Examiner* — Yun Qian
(74) *Attorney, Agent, or Firm* — Lerner, David, Littenberg, Krumholz & Mentlik, LLP

(57) ABSTRACT

The present invention relates to a novel ligand compound represented by Formula 1 and a novel transition metal compound represented by Formula 2, and the novel ligand compound and transition metal compound according to the present invention has high comonomer incorporation effect in the preparation of an olefinic polymer having a low density and a high molecular weight, and thus can be usefully used as a catalyst for a polymerization reaction.

3 Claims, No Drawings

COMPOUND AND TRANSITION METAL COMPOUND

CROSS-REFERENCE TO RELATED APPLICATION

This application is a divisional of U.S. application Ser. No. 15/749,309, filed Jan. 31, 2018 which is a national phase entry under 35 U.S.C. § 371 of International Application No. PCT/KR2017/001503, filed Feb. 10, 2017, which claims priority to Korean Patent Application No. 10-2016-0016517, filed Feb. 12, 2016 and Korean Patent Application No. 10-2017-0018307, filed Feb. 9, 2017, the disclosures of which are incorporated herein by reference

TECHNICAL FIELD

The present invention relates to a novel ligand compound and transition metal compound.

BACKGROUND ART

Metallocene catalysts for olefin polymerization have been developed for a long time. Metallocene compounds are generally activated by aluminoxane, borane, borate or other activators and used. For example, aluminoxane is used as an activator for a metallocene compound having a ligand including a cyclopentadienyl group and two sigma chloride ligands. A case in which, when a chloride group of the metallocene compound is replaced with another ligand (e.g., a benzyl or trimethylsilyl methyl group (—CH$_2$SiMe$_3$)), the effect of increasing catalytic activity or the like is exhibited, has been reported.

[Me$_2$Si(Me$_4$C$_5$)NtBu]TiCl$_2$ (constrained-geometry catalyst, CGC) was disclosed by U.S. Pat. No. 5,064,802 of the Dow Co. in the early 1990s, and excellent aspects of the CGC in the copolymerization reaction of ethylene and an alpha-olefin may be summarized in the following two points when compared to known metallocene catalysts: (1) Even at a high polymerization temperature, high activity is shown and a polymer having a high molecular weight is produced, and (2) the copolymerization degree of an alpha-olefin having large steric hindrance such as 1-hexene and 1-octene is excellent.

Further, as various properties of the CGC during a polymerization reaction are gradually known, efforts of synthesizing the derivatives thereof and using them as a polymerization catalyst have been actively conducted in academia and industry.

As one approach, the synthesis of a metal compound introducing various bridges instead of a silicon bridge and a nitrogen substituent and the polymerization thereof has been conducted. In representative metal compounds known until now, phosphorous, ethylene or propylene, methylidene or methylene bridges are introduced instead of the silicon bridge of a CGC structure, but excellent results in terms of polymerization activity, copolymerization performance or the like could not be obtained by applying to ethylene polymerization or copolymerization with an alpha-olefin when compared to those obtained by applying the CGC.

As another approach, many compounds including an oxido ligand instead of the amido ligand of the CGC have been synthesized, and attempts at polymerization using them have been conducted to some extent.

Further, a variety of asymmetric non-crosslinked metallocenes have been developed. For example, (cyclopentadienyl)(indenyl) and (cyclopentadienyl)(fluorenyl) metallocene, (substituted indenyl)(cyclopentadienyl) metallocene and the like are known.

However, in view of commercial use, the catalyst compositions of the non-crosslinked metallocenes do not sufficiently exhibit the polymerization activity of olefins, and polymerization of a polyolefin having a high molecular weight is difficult.

DISCLOSURE

Technical Problem

An object of the present invention is to provide a novel ligand compound.

Another object of the present invention is to provide a novel transition metal compound.

Technical Solution

In order to solve the above problem, the present invention provides a ligand compound represented by the following Formula 1:

[Formula 1]

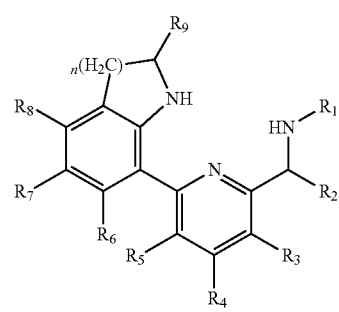

in Formula 1, R$_1$ to R$_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the R$_1$ to R$_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, an alkenyl having 2 to 20 carbon atoms or an aryl having 6 to 20 carbon atoms; and n is 1 or 2.

Further, in order to solve another problem, the present invention provides a transition metal compound represented by the following Formula 2:

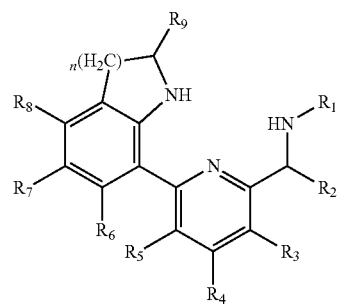

[Formula 1]

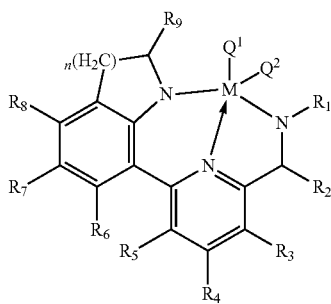

[Formula 2]

in Formula 1, $R_1$ to $R_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, an alkenyl having 2 to 20 carbon atoms or an aryl having 6 to 20 carbon atoms; and n is 1 or 2.

Further, in Formula 1, $R_1$ to $R_9$ each may independently represent hydrogen, an alkyl having 1 to 20 carbon atoms, an aryl having 6 to 20 carbon atoms, an alkylaryl having 7 to 20 carbon atoms, or an arylalkyl having 7 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; and the aliphatic ring or aromatic ring may be substituted with a halogen, an alkyl having 1 to 20 carbon atoms, or an aryl having 6 to 20 carbon atoms.

In an example of the present invention, the ligand compound of Formula 1 may be one of the following compounds:

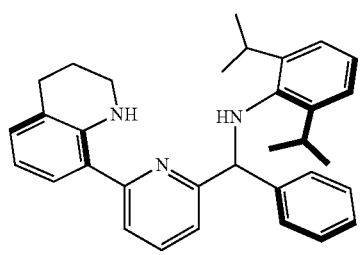

[Formula 1a]

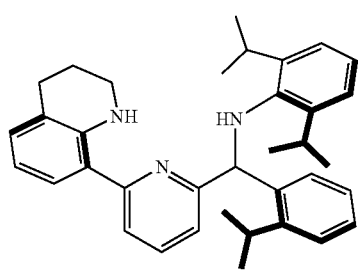

[Formula 1b]

in Formula 2, $R_1$ to $R_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, an alkenyl having 2 to 20 carbon atoms or an aryl having 6 to 20 carbon atoms; and n is 1 or 2; $Q^1$ and $Q^2$ each independently represent hydrogen, a halogen, an alkyl having 1 to 20 carbon atoms, an alkenyl having 2 to 20 carbon atoms, an aryl having 6 to 20 carbon atoms, an alkylaryl having 6 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms; and M is Ti, Zr or Hf.

Advantageous Effects

The novel ligand compound and transition metal compound according to the present invention has a high comonomer incorporation effect in the preparation of an olefinic polymer having a low density and a high molecular weight, and thus can be usefully used as a catalyst for polymerization reactions.

BEST MODE FOR CARRYING OUT THE INVENTION

Hereinafter, the present invention will be described in more detail to allow for a clearer understanding of the present invention.

It will be understood that words or terms used in the specification and claims shall not be interpreted as the meaning defined in commonly used dictionaries. It will be further understood that the words or terms should be interpreted as having a meaning that is consistent with their meaning in the context of the relevant art and the technical idea of the invention, based on the principle that an inventor may properly define the meaning of the words or terms to best explain the invention.

A ligand compound of the present invention is represented by the following Formula 1.

-continued

[Formula 1c]

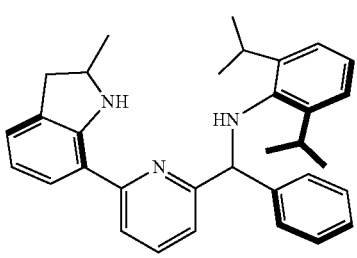

[Formula 1d]

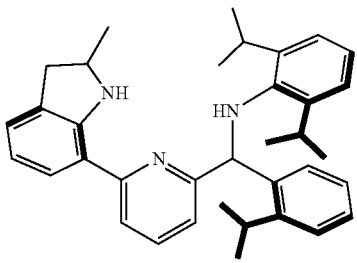

[Formula 1e]

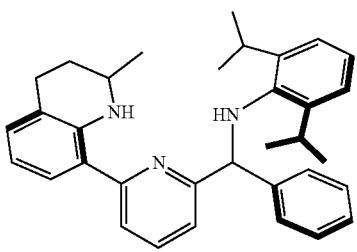

[Formula 1f]

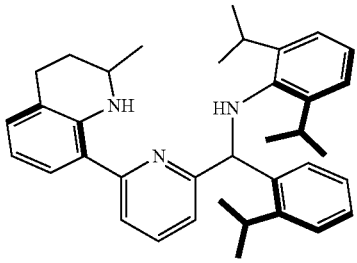

[Formula 1g]

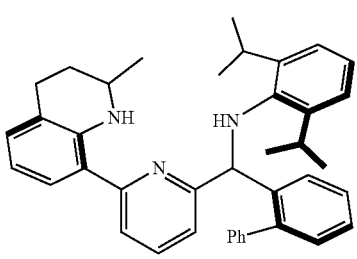

[Formula 1h]

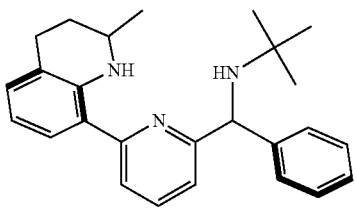

-continued

[Formula 1i]

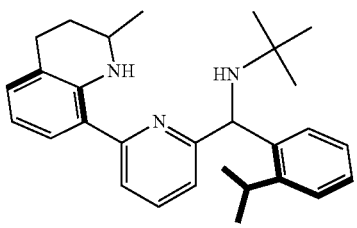

[Formula 1j]

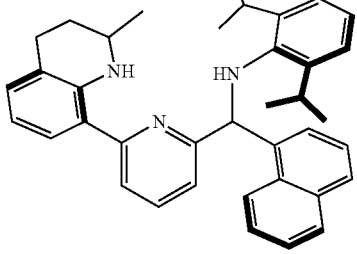

[Formula 1k]

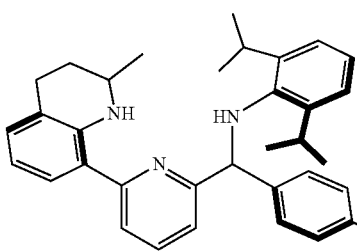

Furthermore, the transition metal compound according to the present invention may be represented by the following Formula 2.

[Formula 2]

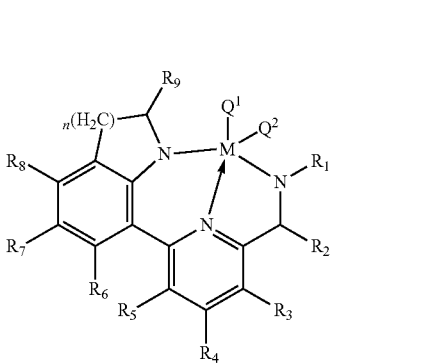

in Formula 2, $R_1$ to $R_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, an alkenyl having 2 to 20 carbon atoms or an aryl having 6 to 20 carbon atoms; n is 1 or 2; $Q^1$ and $Q^2$ each independently represent hydrogen, a halogen, an alkyl having 1 to 20 carbon atoms, an alkenyl having 2 to 20 carbon atoms, an aryl having 6 to 20 carbon atoms, an alkylaryl having 6 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms; and M is Ti, Zr or Hf.

Further, in Formula 2, $Q^1$ and $Q^2$ each may independently represent hydrogen, a halogen, an alkyl having 1 to 20 carbon atoms, an aryl having 6 to 20 carbon atoms, an alkylaryl having 6 to 20 carbon atoms, or an arylalkyl having 7 to 20 carbon atoms.

Further, in Formula 2, $R_1$ to $R_9$ each may independently represent hydrogen, an alkyl having 1 to 20 carbon atoms, an aryl having 6 to 20 carbon atoms, an alkylaryl having 7 to 20 carbon atoms, or an arylalkyl having 7 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, or an aryl having 6 to 20 carbon atoms.

In an example of the present invention, the compound of Formula 2 may be one of the following compounds:

[Formula 2a]

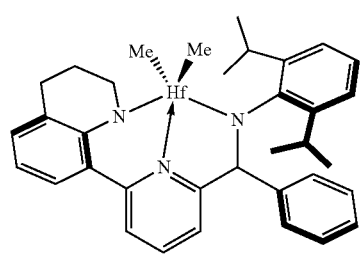

[Formula 2b]

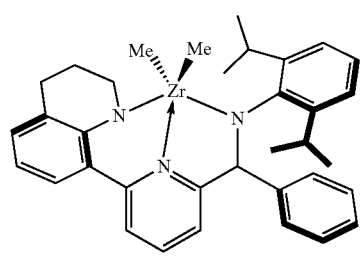

[Formula 2c]

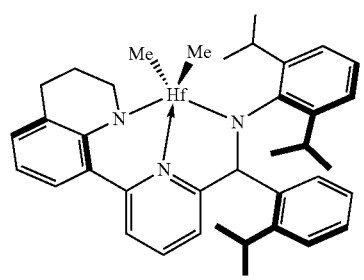

[Formula 2d]

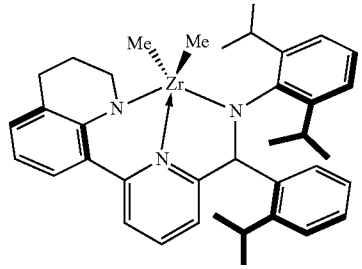

[Formula 2e]

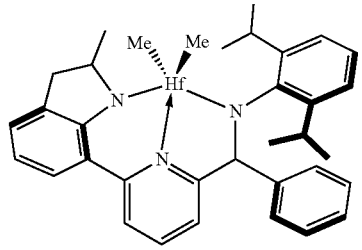

[Formula 2f]

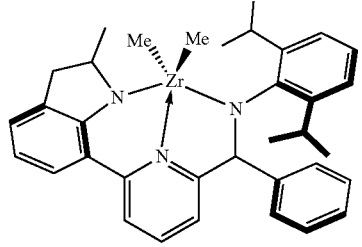

[Formula 2g]

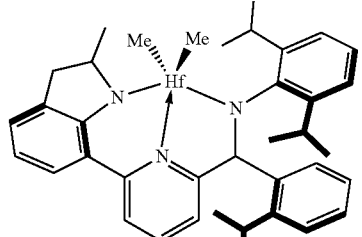

[Formula 2h]

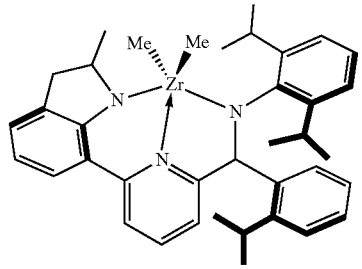

[Formula 2i]

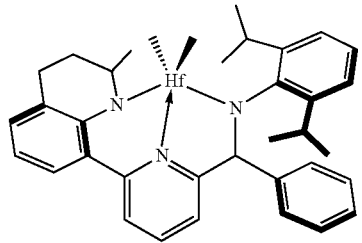

[Formula 2j]
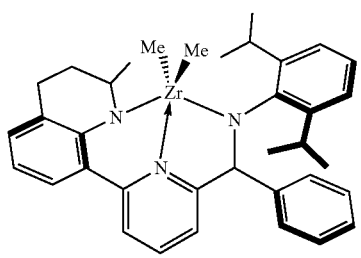
[Formula 2k]
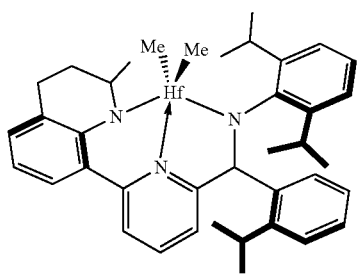
[Formula 2l]
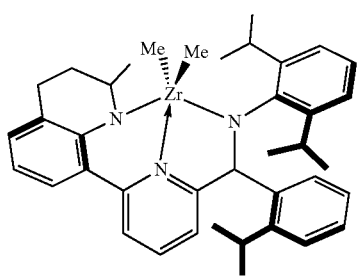
[Formula 2m]
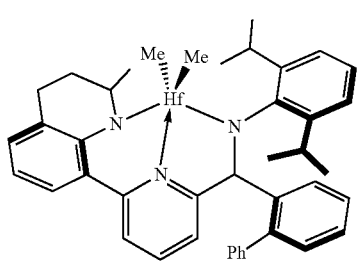
[Formula 2n]
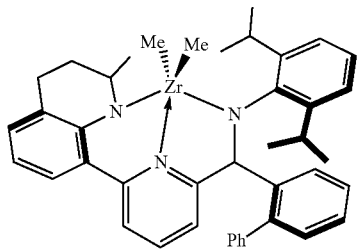
[Formula 2o]
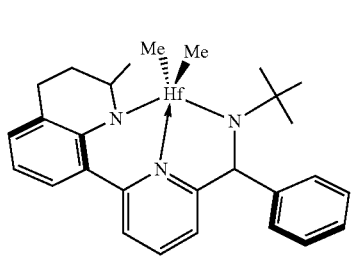
[Formula 2p]
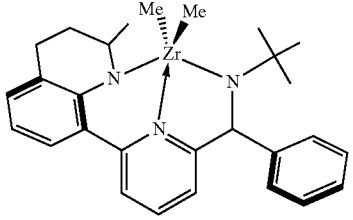
[Formula 2q]
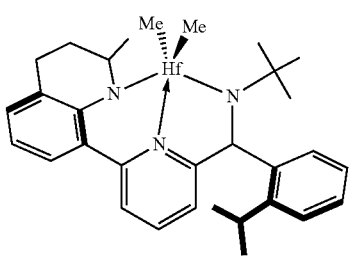
[Formula 2r]
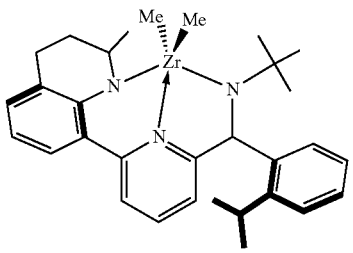
[Formula 2s]
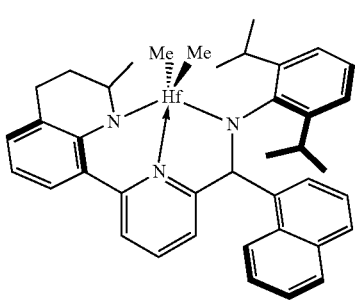
[Formula 2t]
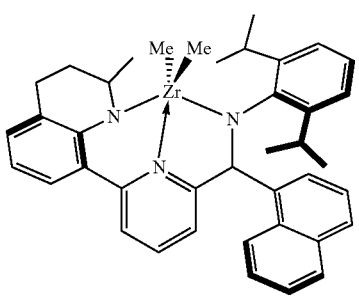
[Formula 2u]
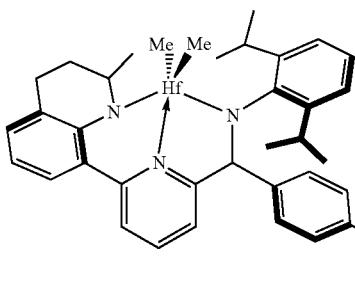

[Formula 2v]

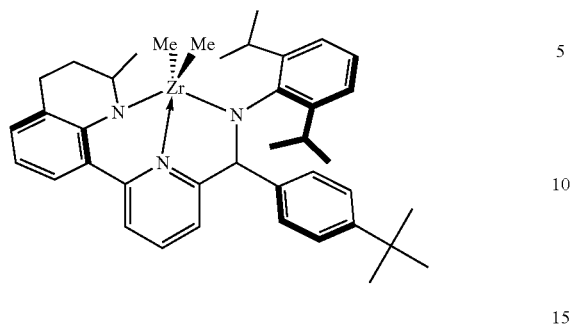

Further, in addition to Formulas 2a to 2v, each of specific substituents of the compound of Formula 2 and a combination thereof are shown in the following Tables 1 to 5.

TABLE 1

| no | n | M | $Q^1$ | $Q^2$ | $R_1$ | $R_2$ | $R_3$ | $R_4$ | $R_5$ | $R_6$ | $R_7$ | $R_8$ | $R_9$ |
|---|---|---|---|---|---|---|---|---|---|---|---|---|---|
| 1 | 1 | Hf | Cl | Cl | Diisopropylphenyl | Phenyl | H | H | H | H | H | H | —$CH_3$ |
| 2 | 1 | Hf | Cl | Cl | Diisopropylphenyl | Isopropylphenyl | H | H | H | H | H | H | —$CH_3$ |
| 3 | 1 | Zr | Cl | Cl | Diisopropylphenyl | Phenyl | H | H | H | H | H | H | —$CH_3$ |
| 4 | 1 | Zr | Cl | Cl | Diisopropyphenyll | Isopropylphenyl | H | H | H | H | H | H | —$CH_3$ |
| 5 | 2 | Zr | Cl | Cl | Diisopropylphenyl | Phenyl | H | H | H | H | H | H | H |
| 6 | 2 | Zr | Cl | Cl | Diisopropylphenyl | Isopropylphenyl | H | H | H | H | H | H | H |
| 7 | 2 | Zr | Cl | Cl | Diisopropylphenyl | Phenyl | H | H | H | H | H | H | —$CH_3$ |
| 8 | 2 | Zr | Cl | Cl | Diisopropylphenyl | Isopropylphenyl | H | H | H | H | H | H | —$CH_3$ |
| 9 | 2 | Zr | Cl | Cl | Diisopropylphenyl | Biphenyl | H | H | H | H | H | H | —$CH_3$ |
| 10 | 2 | Zr | Cl | Cl | t-butyl | Phenyl | H | H | H | H | H | H | —$CH_3$ |
| 11 | 2 | Zr | Cl | Cl | t-butyl | Isopropylphenyl | H | H | H | H | H | H | —$CH_3$ |
| 12 | 2 | Zr | Cl | Cl | Diisopropylphenyl | Naphthyl | H | H | H | H | H | H | —$CH_3$ |
| 13 | 2 | Zr | Cl | Cl | Diisopropylphenyl | t-butylphenyl | H | H | H | H | H | H | —$CH_3$ |
| 14 | 2 | Hf | Cl | Cl | Diisopropylphenyl | Phenyl | H | H | H | H | H | H | H |
| 15 | 2 | Hf | Cl | Cl | Diisopropylphenyl | Isopropylphenyl | H | H | H | H | H | H | H |
| 16 | 2 | Hf | Cl | Cl | Diisopropylphenyl | Phenyl | H | H | H | H | H | H | —$CH_3$ |
| 17 | 2 | Hf | Cl | Cl | Diisopropylphenyl | Isopropylphenyl | H | H | H | H | H | H | —$CH_3$ |
| 18 | 2 | Hf | Cl | Cl | Diisopropylphenyl | Biphenyl | H | H | H | H | H | H | —$CH_3$ |
| 19 | 2 | Hf | Cl | Cl | t-butyl | Phenyl | H | H | H | H | H | H | —$CH_3$ |
| 20 | 2 | Hf | Cl | Cl | t-butyl | Isopropylphenyl | H | H | H | H | H | H | —$CH_3$ |
| 21 | 2 | Hf | Cl | Cl | Diisopropylphenyl | Naphthyl | H | H | H | H | H | H | —$CH_3$ |
| 22 | 2 | Hf | Cl | Cl | Diisopropylphenyl | t-butylphenyl | H | H | H | H | H | H | —$CH_3$ |

TABLE 2

| no | n | M | $Q^1$ | $Q^2$ | $R_1$ | $R_2$ | $R_3$ | $R_4$ | $R_5$ | $R_6$ | $R_7$ | $R_8$ | $R_9$ |
|---|---|---|---|---|---|---|---|---|---|---|---|---|---|
| 23 | 1 | Hf | Me | Me | Phenyl | Diisopropylphenyl | H | H | H | H | H | H | —$CH_3$ |
| 24 | 1 | Hf | Me | Me | Isopropylphenyl | Diisopropylphenyl | H | H | H | H | H | H | —$CH_3$ |
| 25 | 1 | Hf | Me | Me | Phenyl | Diisopropylphenyl | H | H | H | H | H | H | H |
| 26 | 1 | Hf | Me | Me | Isopropylphenyl | Diisopropylphenyl | H | H | H | H | H | H | H |
| 27 | 1 | Hf | Me | Me | Phenyl | Phenyl | H | H | H | H | H | H | —$CH_3$ |
| 28 | 1 | Hf | Me | Me | Diisopropylphenyl | Diisopropylphenyl | H | H | H | H | H | H | —$CH_3$ |
| 29 | 1 | Hf | Me | Me | Isopropylphenyl | Isopropylphenyl | H | H | H | H | H | H | —CH3 |
| 30 | 1 | Hf | Me | Me | Isopropylphenyl | Phenyl | H | H | H | H | H | H | —$CH_3$ |
| 31 | 1 | Hf | Me | Me | Phenyl | Isopropylphenyl | H | H | H | H | H | H | —$CH_3$ |
| 32 | 1 | Hf | Me | Me | Phenyl | Phenyl | H | H | H | H | H | H | H |
| 33 | 1 | Hf | Me | Me | Diisopropylphenyl | Diisopropylphenyl | H | H | H | H | H | H | H |
| 34 | 1 | Hf | Me | Me | Isopropylphenyl | Isopropylphenyl | H | H | H | H | H | H | H |
| 35 | 1 | Hf | Me | Me | Isopropylphenyl | Phenyl | H | H | H | H | H | H | H |
| 36 | 1 | Hf | Me | Me | Phenyl | Isopropylphenyl | H | H | H | H | H | H | H |
| 37 | 1 | Hf | Me | Me | t-butyl | Phenyl | H | H | H | H | H | H | —$CH_3$ |
| 38 | 1 | Hf | Me | Me | t-butyl | Isopropylphenyl | H | H | H | H | H | H | —$CH_3$ |
| 39 | 1 | Hf | Me | Me | Diisopropylphenyl | Naphthyl | H | H | H | H | H | H | —$CH_3$ |
| 40 | 1 | Hf | Me | Me | Diisopropylphenyl | t-butylphenyl | H | H | H | H | H | H | —$CH_3$ |

TABLE 2-continued

| no | n | M | Q¹ | Q² | R₁ | R₂ | R₃ | R₄ | R₅ | R₆ | R₇ | R₈ | R₉ |
|---|---|---|---|---|---|---|---|---|---|---|---|---|---|
| 41 | 1 | Hf | Me | Me | t-butyl | Phenyl | H | H | H | H | H | H | H |
| 42 | 1 | Hf | Me | Me | t-butyl | Isopropylphenyl | H | H | H | H | H | H | H |
| 43 | 1 | Hf | Me | Me | Diisopropylphenyl | Naphthyl | H | H | H | H | H | H | H |

TABLE 3

| no | n | M | Q¹ | Q² | R₁ | R₂ | R₃ | R₄ | R₅ | R₆ | R₇ | R₈ | R₉ |
|---|---|---|---|---|---|---|---|---|---|---|---|---|---|
| 44 | 1 | Hf | Cl | Cl | Diisopropylphenyl | t-butylphenyl | H | H | H | H | H | H | H |
| 45 | 1 | Hf | Cl | Cl | Phenyl | Diisopropylphenyl | H | H | H | H | H | H | —CH₃ |
| 46 | 1 | Hf | Cl | Cl | Isopropylphenyl | Diisopropylphenyl | H | H | H | H | H | H | —CH₃ |
| 47 | 1 | Hf | Cl | Cl | Phenyl | Diisopropylphenyl | H | H | H | H | H | H | H |
| 48 | 1 | Hf | Cl | Cl | Isopropylphenyl | Diisopropylphenyl | H | H | H | H | H | H | H |
| 49 | 1 | Hf | Cl | Cl | Phenyl | Phenyl | H | H | H | H | H | H | —CH₃ |
| 50 | 1 | Hf | Cl | Cl | Diisopropylphenyl | Diisopropylphenyl | H | H | H | H | H | H | —CH₃ |
| 51 | 1 | Hf | Cl | Cl | Isopropylphenyl | Isopropylphenyl | H | H | H | H | H | H | —CH₃ |
| 52 | 1 | Hf | Cl | Cl | Isopropylphenyl | Phenyl | H | H | H | H | H | H | —CH₃ |
| 53 | 1 | Hf | Cl | Cl | Phenyl | Isopropylphenyl | H | H | H | H | H | H | —CH₃ |
| 54 | 1 | Hf | Cl | Cl | Phenyl | Phenyl | H | H | H | H | H | H | H |
| 55 | 1 | Hf | Cl | Cl | Diisopropylphenyl | Diisopropylphenyl | H | H | H | H | H | H | H |
| 56 | 1 | Hf | Cl | Cl | Isopropylphenyl | Isopropylphenyl | H | H | H | H | H | H | H |
| 57 | 1 | Hf | Cl | Cl | Isopropylphenyl | Phenyl | H | H | H | H | H | H | H |
| 58 | 1 | Hf | Cl | Cl | Phenyl | Isopropylphenyl | H | H | H | H | H | H | H |
| 59 | 1 | Hf | Cl | Cl | t-butyl | Phenyl | H | H | H | H | H | H | —CH₃ |
| 60 | 1 | Hf | Cl | Cl | t-butyl | Isopropylphenyl | H | H | H | H | H | H | —CH₃ |
| 61 | 1 | Hf | Cl | Cl | Diisopropylphenyl | Naphthyl | H | H | H | H | H | H | —CH₃ |
| 62 | 1 | Hf | Cl | Cl | Diisopropylphenyl | t-butylphenyl | H | H | H | H | H | H | —CH₃ |
| 63 | 1 | Hf | Cl | Cl | t-butyl | Phenyl | H | H | H | H | H | H | H |
| 64 | 1 | Hf | Cl | Cl | t-butyl | Isopropylphenyl | H | H | H | H | H | H | H |
| 65 | 1 | Hf | Cl | Cl | Diisopropylphenyl | Naphthyl | H | H | H | H | H | H | H |
| 66 | 1 | Hf | Cl | Cl | Diisopropylphenyl | t-butylphenyl | H | H | H | H | H | H | H |

TABLE 4

| no | n | M | Q¹ | Q² | R₁ | R₂ | R₃ | R₄ | R₅ | R₆ | R₇ | R₈ | R₉ |
|---|---|---|---|---|---|---|---|---|---|---|---|---|---|
| 67 | 2 | Hf | Me | Me | Phenyl | Diisopropylphenyl | H | H | H | H | H | H | —CH₃ |
| 68 | 2 | Hf | Me | Me | Isopropylphenyl | Diisopropylphenyl | H | H | H | H | H | H | —CH₃ |
| 69 | 2 | Hf | Me | Me | Phenyl | Diisopropylphenyl | H | H | H | H | H | H | H |
| 70 | 2 | Hf | Me | Me | Isopropylphenyl | Diisopropylphenyl | H | H | H | H | H | H | H |
| 71 | 2 | Hf | Me | Me | Phenyl | Phenyl | H | H | H | H | H | H | —CH₃ |
| 72 | 2 | Hf | Me | Me | Diisopropylphenyl | Diisopropylphenyl | H | H | H | H | H | H | —CH₃ |
| 73 | 2 | Hf | Me | Me | Isopropylphenyl | Isopropylphenyl | H | H | H | H | H | H | —CH₃ |
| 74 | 2 | Hf | Me | Me | Isopropylphenyl | Phenyl | H | H | H | H | H | H | —CH₃ |
| 75 | 2 | Hf | Me | Me | Phenyl | Isopropylphenyl | H | H | H | H | H | H | —CH₃ |
| 76 | 2 | Hf | Me | Me | Phenyl | Phenyl | H | H | H | H | H | H | H |
| 77 | 2 | Hf | Me | Me | Diisopropylphenyl | Diisopropylphenyl | H | H | H | H | H | H | H |
| 78 | 2 | Hf | Me | Me | Isopropylphenyl | Isopropylphenyl | H | H | H | H | H | H | H |
| 79 | 2 | Hf | Me | Me | Isopropylphenyl | Phenyl | H | H | H | H | H | H | H |
| 80 | 2 | Hf | Me | Me | Phenyl | Isopropylphenyl | H | H | H | H | H | H | H |
| 81 | 2 | Hf | Me | Me | t-butyl | Phenyl | H | H | H | H | H | H | —CH₃ |
| 82 | 2 | Hf | Me | Me | t-butyl | Isopropylphenyl | H | H | H | H | H | H | —CH₃ |
| 83 | 2 | Hf | Me | Me | Diisopropylphenyl | Naphthyl | H | H | H | H | H | H | —CH₃ |
| 84 | 2 | Hf | Me | Me | Diisopropylphenyl | t-butylphenyl | H | H | H | H | H | H | —CH₃ |
| 85 | 2 | Hf | Me | Me | t-butyl | Phenyl | H | H | H | H | H | H | H |
| 86 | 2 | Hf | Me | Me | t-butyl | Isopropylphenyl | H | H | H | H | H | H | H |
| 87 | 2 | Hf | Me | Me | Diisopropylphenyl | Naphthyl | H | H | H | H | H | H | H |
| 88 | 2 | Hf | Me | Me | Diisopropylphenyl | t-butylphenyl | H | H | H | H | H | H | H |
| 89 | 2 | Hf | Cl | Cl | Phenyl | Diisopropylphenyl | H | H | H | H | H | H | —CH₃ |
| 90 | 2 | Hf | Cl | Cl | Isopropylphenyl | Diisopropylphenyl | H | H | H | H | H | H | —CH₃ |

TABLE 5

| no | n | M | $Q^1$ | $Q^2$ | $R_1$ | $R_2$ | $R_3$ | $R_4$ | $R_5$ | $R_6$ | $R_7$ | $R_8$ | $R_9$ |
|---|---|---|---|---|---|---|---|---|---|---|---|---|---|
| 91 | 2 | Hf | Cl | Cl | Phenyl | Diisopropylphenyl | H | H | H | H | H | H | H |
| 92 | 2 | Hf | Cl | Cl | Isopropylphenyl | Diisopropylphenyl | H | H | H | H | H | H | H |
| 93 | 2 | Hf | Cl | Cl | Phenyl | Phenyl | H | H | H | H | H | H | —CH₃ |
| 94 | 2 | Hf | Cl | Cl | Diisopropylphenyl | Diisopropylphenyl | H | H | H | H | H | H | —CH₃ |
| 95 | 2 | Hf | Cl | Cl | Isopropylphenyl | Isopropylphenyl | H | H | H | H | H | H | —CH₃ |
| 96 | 2 | Hf | Cl | Cl | Isopropylphenyl | Phenyl | H | H | H | H | H | H | —CH₃ |
| 97 | 2 | Hf | Cl | Cl | Phenyl | Isopropylphenyl | H | H | H | H | H | H | —CH₃ |
| 98 | 2 | Hf | Cl | Cl | Phenyl | Phenyl | H | H | H | H | H | H | H |
| 99 | 2 | Hf | Cl | Cl | Diisopropylphenyl | Diisopropylphenyl | H | H | H | H | H | H | H |
| 100 | 2 | Hf | Cl | Cl | Isopropylphenyl | Isopropylphenyl | H | H | H | H | H | H | H |
| 101 | 2 | Hf | Cl | Cl | Isopropylphenyl | Phenyl | H | H | H | H | H | H | H |
| 102 | 2 | Hf | Cl | Cl | Phenyl | Isopropylphenyl | H | H | H | H | H | H | H |
| 103 | 2 | Hf | Cl | Cl | t-butyl | Phenyl | H | H | H | H | H | H | —CH₃ |
| 104 | 2 | Hf | Cl | Cl | t-butyl | Isopropylphenyl | H | H | H | H | H | H | —CH₃ |
| 105 | 2 | Hf | Cl | Cl | Diisopropylphenyl | Naphthyl | H | H | H | H | H | H | —CH₃ |
| 106 | 2 | Hf | Cl | Cl | Diisopropylphenyl | t-butylphenyl | H | H | H | H | H | H | —CH₃ |
| 107 | 2 | Hf | Cl | Cl | t-butyl | Phenyl | H | H | H | H | H | H | H |
| 108 | 2 | Hf | Cl | Cl | t-butyl | Isopropylphenyl | H | H | H | H | H | H | H |
| 109 | 2 | Hf | Cl | Cl | Diisopropylphenyl | Naphthyl | H | H | H | H | H | H | H |
| 110 | 2 | Hf | Cl | Cl | Diisopropylphenyl | t-butylphenyl | H | H | H | H | H | H | H |

The definition of each substituent used in the present specification is described in detail as follows.

The term "halogen" used in the present specification, unless otherwise specified, refers to fluorine, chlorine, bromine and iodine.

The term "alkyl" used in the present specification, unless otherwise specified, refers to a linear or branched hydrocarbon residue.

The term "alkenyl" used in the present specification, unless otherwise specified, refers to a linear or branched alkenyl group.

The branched chain may be an alkyl having 1 to 20 carbon atoms; an alkenyl having 2 to 20 carbon atoms; an aryl having 6 to 20 carbon atoms; an alkylaryl having 7 to 20 carbon atoms; or an arylalkyl having 7 to 20 carbon atoms.

According to an example of the present invention, the silyl group includes trimethyl silyl, triethyl silyl, tripropyl silyl, tributyl silyl, trihexyl silyl, triisopropyl silyl, triisobutyl silyl, triethoxy silyl, triphenyl silyl, tris(trimethylsilyl) silyl, but is not limited thereto.

According to an example of the present invention, the aryl group preferably has 6 to 20 carbon atoms, and specifically includes phenyl, naphthyl, anthracenyl, pyridyl, dimethylanilinyl, anisolyl and the like, but is not limited thereto.

The alkylaryl group refers to an aryl group substituted with the alkyl group.

The arylalkyl group refers to an alkyl group substituted with the aryl group.

The ring (or a heterocyclic group) refers to a monovalent aliphatic or aromatic hydrocarbon group which has a ring atom with 5 to 20 carbon atoms and contains one or more heteroatoms, and may be a single ring or a condensed ring of two or more rings. Further, the heterocyclic group may be unsubstituted or substituted with an alkyl group. Examples thereof include indoline, tetrahydroquinoline and the like, but the present invention is not limited thereto.

The alkylamino group refers to an amino group substituted with the alkyl group, and includes a dimethylamino group, a diethylamino group and the like, but is not limited thereto.

According to an embodiment of the present invention, the aryl group preferably has 6 to 20 carbon atoms, and specifically includes phenyl, naphthyl, anthracenyl, pyridyl, dimethylanilinyl, anisolyl and the like, but is not limited thereto.

The ligand compound of the present invention may be prepared by the following method, and specifically, the ligand compound represented by Formula 1 of the present invention may be prepared by a method including the following steps: (1) reacting a compound of the following Formula 3 with a compound of the following Formula 4 to prepare a compound of the following Formula 5; and (2) reacting the compound of the following Formula 5 with a compound of the following Formula 6 to prepare a compound of the following Formula 1.

[Formula 1]

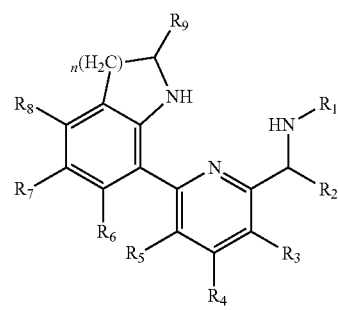

[Formula 3]

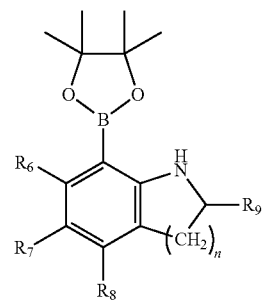

[Formula 4]

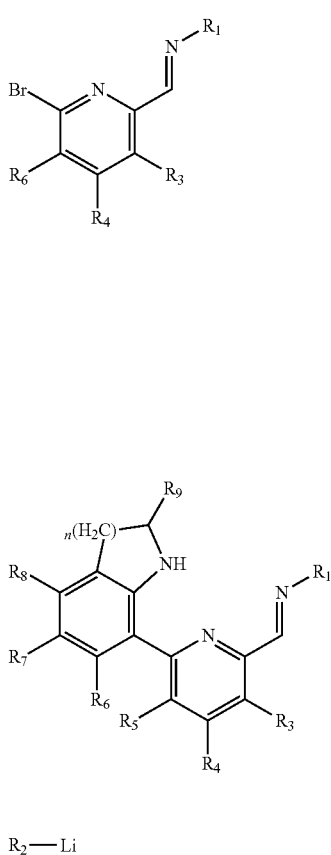

[Formula 5]

[Formula 6]

$R_2$—Li in Formulas 1, and 3 to 6, $R_1$ to $R_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, an alkenyl having 2 to 20 carbon atoms or an aryl having 6 to 20 carbon atoms; and n is 1 or 2.

Further, in Formulas 1, and 3 to 6, $R_1$ to $R_9$ each may independently represent hydrogen, an alkyl having 1 to 20 carbon atoms, an aryl having 6 to 20 carbon atoms, an alkylaryl having 7 to 20 carbon atoms, or an arylalkyl having 7 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; and the aliphatic ring or aromatic ring may be substituted with a halogen, an alkyl having 1 to 20 carbon atoms, or an aryl having 6 to 20 carbon atoms.

(1) Step of Reacting Compound of Formula 3 with Compound of Formula 4 to Prepare Compound of Formula 5

[Reaction Formula 1]

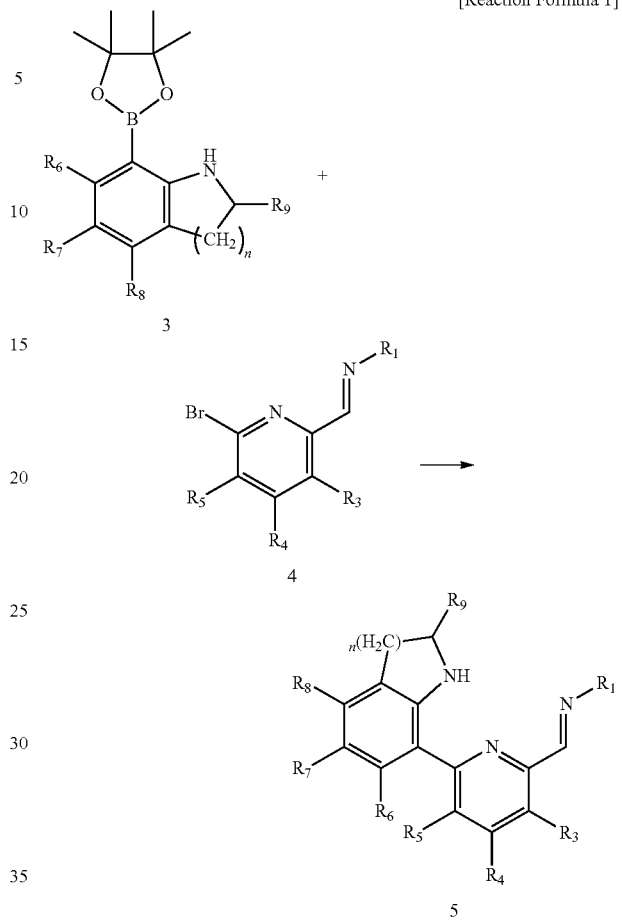

In Step (1), a compound of Formula 5 is prepared by reacting a compound of Formula 3 with a compound of Formula 4.

The reaction of Step (1) may be carried out in the presence of a palladium catalyst under basic conditions, and the reaction may be carried out in an organic solvent such as toluene.

The palladium catalyst may be one or more selected from the group consisting of tetrakis(triphenylphosphine) palladium [Pd(PPh$_3$)$_4$], palladium chloride (PdCl$_2$), palladium acetate (Pd(OAc)$_2$), bis(dibenzylideneacetone) palladium (Pd(dba)$_2$) and Pd(tBu$_3$P$_2$).

A type of a base for forming the basic conditions is not particularly limited, and specific examples thereof include tBuOLi, tribasic potassium (K$_3$PO$_4$), potassium carbonate (K$_2$CO$_3$), cesium carbonate (Cs$_2$CO$_3$), potassium fluoride (KF), sodium fluoride (NaF), cesium fluoride (CsF), tetrabutylammonium fluoride (TBAF) or a mixture thereof.

The reaction of Step (1) may be carried out by a method of reacting in a temperature range of 0 to 140° C., specifically from 40 to 100° C. for 1 to 48 hours, specifically 2 to 12 hours.

The compound of Formula 3 and the compound of Formula 4 each may be previously added to separate solvents and then mixed again, and a palladium catalyst may be added thereto after mixing. For example, the compound of Formula 3 may be added to a mixed solvent of water and alcohol such as ethanol, and the compound of Formula 4 may be added to a solvent such as toluene.

Here, the compound of Formula 3 may be prepared by a reaction represented by the following Reaction Formula 2.

[Reaction Formula 2]

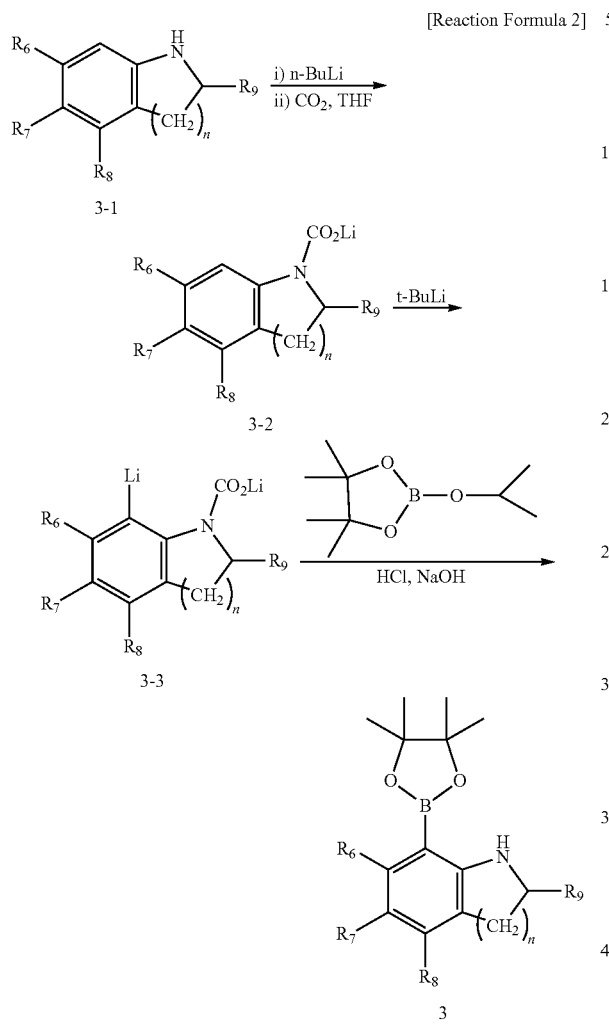

In Reaction Formula 2, $R_6$ to $R_9$ and n are as defined in Formula 3.

A compound of Formula 3-1 is added to an organic solvent such as hexane and n-BuLi is further added in a temperature range of −80 to 0° C. Here, the n-BuLi may be reacted with a compound of Formula 3-1 in a molar ratio of 1:1 to 1:2, and specifically, in a molar ratio of 1:1.1 to 1:1.2. After n-BuLi is added, a mixture is reacted at room temperature for 1 to 48 hours and filtered, a solvent is added to the obtained compound, $CO_2$ is bubbled into the compound at a temperature of −160 to −20° C., and thereby a compound of Formula 3-2 may be obtained. A compound of Formula 3-3 may be obtained by adding t-BuLi to the obtained compound of Formula 3-2 and performing a reaction in a temperature range of −80 to 0° C. After 2-isopropyloxy-4,4,5,5-tetramethyl-1,3,2-dioxaborolane is added to the compound of Formula 3-3 at a temperature of −150 to −20° C., the reaction is allowed to proceed by gradually raising the temperature to room temperature, and thereby a compound of Formula 3 may be obtained. Here, a process of adding HCl and ethyl acetate (EA), washing an organic layer with NaOH and $NaHCO_3$, and then dehydration with $MgSO_4$ may be performed.

(2) Step of Reacting Compound of Formula 5 with Compound of Formula 6 to Prepare Compound of Formula 1

[Reaction Formula 3]

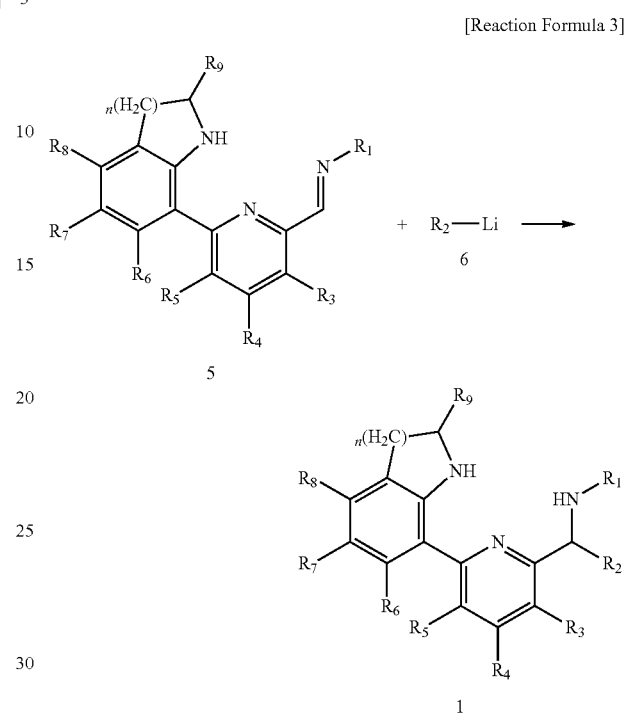

In Step (2), a compound of Formula 1 is prepared by reacting a compound of Formula 5 with a compound of Formula 6.

In Step (2), a compound of Formula 5 is reacted with an organolithium compound of Formula 6 to introduce $R_2$ into Formula 5.

In Step (2), the compound of Formula 5 and the compound of Formula 6 may be reacted in a molar ratio of 1:1 to 1:3, and specifically in a molar ratio of 1:1 to 1:2.

The reaction of Step (2) may be carried out by a method of adding the compound of Formula 6 to the compound of Formula 5 to react in a temperature range of −160 to −20° C., and specifically, may be carried out by a method of adding the compound of Formula 6 to the compound of Formula 5 to react in a temperature range of −120 to −40° C. The reaction may be carried out in an organic solvent such as diethyl ether, and quenched with $NH_4Cl$ or the like when the reaction is completed.

The compound of Formula 1 prepared through Steps (1) and (2) may be further subjected to Step (3) of recrystallization, and thus the method of preparing the transition metal compound according to an example of the present invention may further include Step (3) of recrystallizing the compound of Formula 1 after Step (2).

The recrystallization may be performed using an organic solvent such as toluene as a reaction solvent, and purified through recrystallization to obtain a pure compound of Formula 1.

Further, the transition metal compound represented by Formula 2 of the present invention may be prepared by a method including the following steps: (a) reacting a ligand compound of Formula 1 with an organolithium compound to prepare a compound of Formula 7; and (b) reacting a compound of the following Formula 7 with a compound of the following Formula 8 to prepare a compound of the following Formula 2.

[Formula 1]

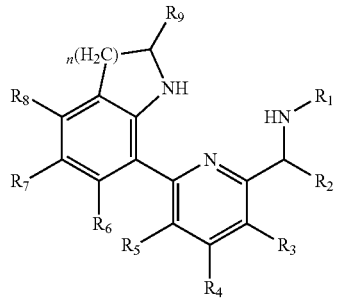

[Formula 2]

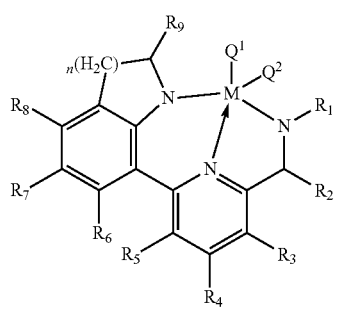

[Formula 7]

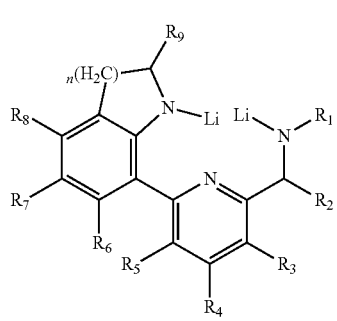

[Formula 8]

$MQ^1Q^2X_2$

Where in Formulas, $R_1$ to $R_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, an alkenyl having 2 to 20 carbon atoms or an aryl having 6 to 20 carbon atoms; n is 1 or 2;

$Q^1$ and $Q^2$ each independently represent hydrogen, a halogen, an alkyl having 1 to 20 carbon atoms, an alkenyl having 2 to 20 carbon atoms, an aryl having 6 to 20 carbon atoms, an alkylaryl having 6 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms;

X is a halogen; and

M is Ti, Zr or Hf.

Further, $R_1$ to $R_9$ each may independently represent hydrogen, an alkyl having 1 to 20 carbon atoms, an aryl having 6 to 20 carbon atoms, an alkylaryl having 7 to 20 carbon atoms, or an arylalkyl having 7 to 20 carbon atoms; two or more adjacent groups of $R_1$ to $R_8$ may be connected to each other to form an aliphatic ring having 5 to 20 carbon atoms or an aromatic ring having 6 to 20 carbon atoms; the aliphatic ring or aromatic ring may be substituted with a halogen, an alkyl having 1 to 20 carbon atoms, or an aryl having 6 to 20 carbon atoms.

Further, a method of preparing the transition metal compound of the present invention may include a step of further reacting a compound of Formula 2 with a Grignard reagent of the following Formula 9.

QMgBr                                    [Formula 9]

in Formula 9, Q is hydrogen, an alkyl having 1 to 20 carbon atoms, an alkenyl having 2 to 20 carbon atoms, an aryl having 6 to 20 carbon atoms, an alkylaryl having 6 to 20 carbon atoms, an arylalkyl having 7 to 20 carbon atoms, an alkylamido having 1 to 20 carbon atoms, an arylamido having 6 to 20 carbon atoms, or an alkylidene having 1 to 20 carbon atoms.

Here, $Q^1$, $Q^2$ or both of them may be halogens in the compound of Formula 2 which reacts with the Grignard reagent of Formula 9. That is, when $Q^1$, $Q^2$, or both of them of Formula 8 are halogens, a compound in which $Q^1$, $Q^2$, or both of them bonded to M in Formula 2 are halogens is prepared. In this case, $Q^1$, $Q^2$, or both of them in Formula 2 may be halogens substituted with Q by further reaction with the Grignard reagent of Formula 9.

(a) Step of Reacting Compound of Formula 1 with Organolithium Compound to Prepare Compound of Formula 7

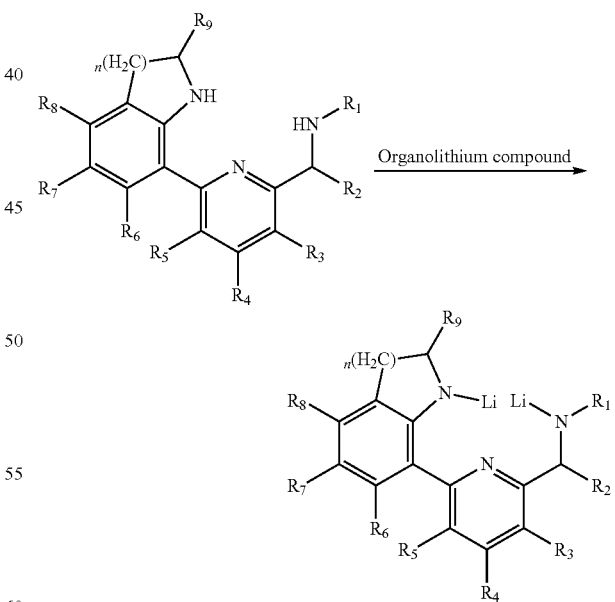

In Step (a), a compound of Formula 7 is prepared by reacting a compound of Formula 1 with an organolithium compound.

In Step (1), the compound of Formula 1 and the organolithium compound may be reacted in a molar ratio of 1:1 to 1:3, and specifically in a molar ratio of 1:1 to 1:2.

The reaction of Step (1) may be carried out in an organic solvent such as diethoxyethane or ether, and may be carried out by adding the organolithium compound to the compound of Formula 1 in an organic solvent.

The organolithium compound may be one or more selected from the group consisting of n-butyllithium, sec-butyllithium, methyllithium, ethyllithium, isopropyllithium, cyclohexyllithium, allyllithium, vinyllithium, phenyllithium and benzyllithium.

The reaction of Step (a) may be carried out by a method of adding the organolithium compound to the compound of Formula 1 in a temperature range of −78 to 0° C. and performing a reaction for 1 to 6 hours, specifically 1 to 4 hours. Here, the reaction temperature may be less than 20° C., and specifically, may be in the range of −78 to 0° C.

(b) Step of Reacting Compound of Formula 7 with Compound of Formula 8 to Prepare Compound of Formula 2

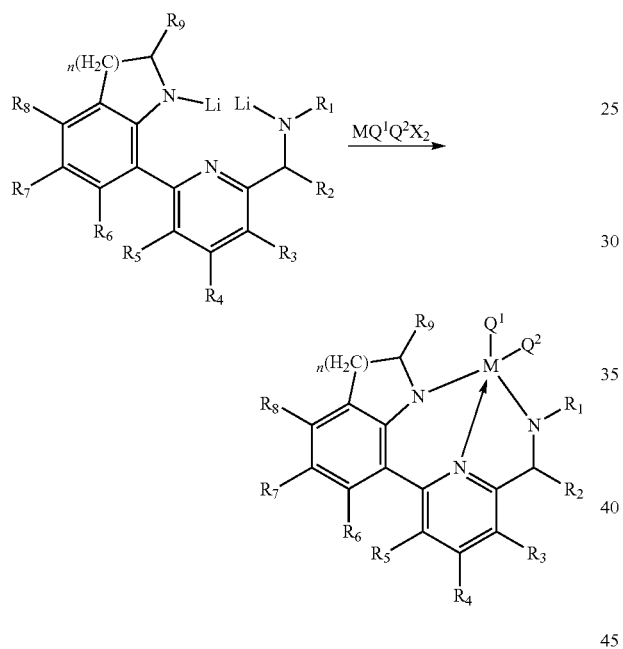

In Step (b), a compound of Formula 2 is prepared by reacting a compound of Formula 7 obtained by Step (a) with a compound of Formula 8.

In Step (b), the compound of Formula 7 and the compound of Formula 8 may be reacted in a molar ratio of 1:0.8 to 1:1.8, and specifically in a molar ratio of 1:1 to 1:1.2.

The reaction of Step (b) may be carried out by a method of raising the temperature to a temperature ranging from 40 to 140° C., specifically 70 to 120° C., and then performing a reaction for 1 to 48 hours, specifically 1 to 4 hours, and the reaction in Step (a) and Step (b) may be performed in one step.

That is, the reaction of Step (a) and Step (b) may be performed by a method of adding the organolithium compound to the compound of Formula 1 in a temperature range of −20 to 30° C., further adding the compound of Formula 8 thereto, raising the temperature to a temperature ranging from 40 to 140° C., specifically to a temperature ranging from 70 to 120° C., and then performing a reaction for 1 to 48 hours, and specifically for 1 to 4 hours.

Accordingly, the transition metal compound of Formula 2 may be prepared.

Further, when $Q^1$, $Q^2$ or both of them in the transition metal compound of Formula 2 are halogens, the additional reaction with the Grignard reagent of Formula 9 may be performed. Here, the reaction between the transition metal compound of Formula 2 and the Grignard reagent of Formula 9 may be performed according to the known Grignard reaction.

A transition metal compound prepared by the additional reaction may be represented by one of the following Formulas 9a to 9c.

[Formula 9a]

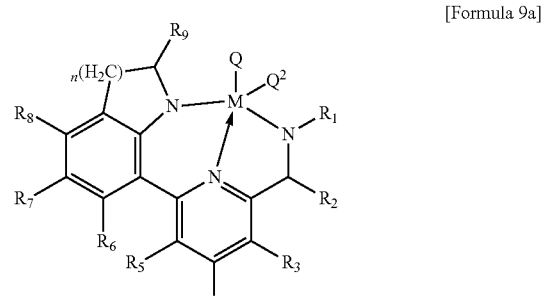

[Formula 9b]

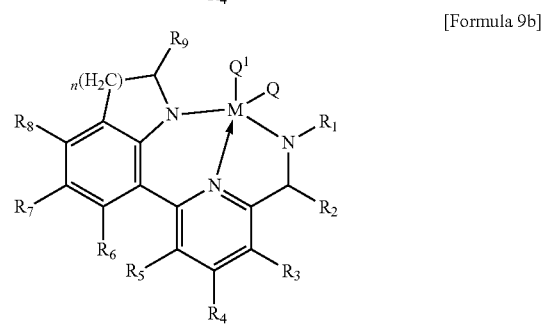

[Formula 9c]

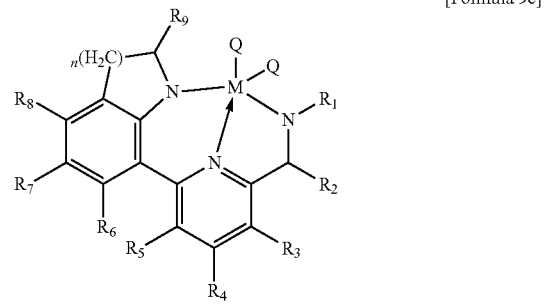

More specifically, the transition metal compound according to the present invention may be used as a catalyst for the polymerization reaction alone or in the form of a composition further including one or more of cocatalyst compounds represented by the following Formulas 10, 11 and 12 in addition to the transition metal compound.

$$—[Al(R_7)—O]_m—$$ [Formula 10]

in Formula 10, $R_7$ may be the same or different from each other and each independently represents a halogen, a hydrocarbon having 1 to 20 carbon atoms or a halogen-substituted hydrocarbon having 1 to 20 carbon atoms, and m is an integer of 2 or more;

$$J(R_7)_3$$ [Formula 11]

in Formula 11, $R_7$ is as defined in Formula 10, and J is aluminum or boron;

$$[E-H]^+[ZA_4]^- \text{ or } [E]^+[ZA_4]^-$$ [Formula 12]

in Formula 12, E is a neutral or cationic Lewis base, H is a hydrogen atom, Z is a Group 13 element, and A may be the same or different from each other and each independently represents an aryl group having 6 to 20 carbon atoms or an alkyl group having 1 to 20 carbon atoms, of which one or more hydrogen atoms are unsubstituted or substituted with a halogen, a hydrocarbon having 1 to 20 carbon atoms, alkoxy, or phenoxy.

Examples of the compound represented by Formula 10 include methyl aluminoxane, ethyl aluminoxane, isobutyl aluminoxane, and butyl aluminoxane, and a more preferable compound is methyl aluminoxane.

Examples of the compound represented by Formula 11 include trimethyl aluminum, triethyl aluminum, triisobutyl aluminum, tripropyl aluminum, tributyl aluminum, dimethylchloroaluminum, triisopropyl aluminum, tri-s-butyl aluminum, tricyclopentyl aluminum, tripentyl aluminum, triisopentyl aluminum, trihexyl aluminum, trioctyl aluminum, ethyl dimethyl aluminum, methyl diethyl aluminum, triphenyl aluminum, tri-p-tolyl aluminum, dimethyl aluminum methoxide, dimethyl aluminum ethoxide, trimethylboron, triethylboron, triisobutylboron, tripropylboron, tributylboron and the like, and a more preferable compound is selected from trimethyl aluminum, triethyl aluminum and triisobutyl aluminum.

Examples of the compound represented by Formula 12 include triethylammonium tetraphenylboron, tributylammonium tetraphenylboron, trimethylammonium tetraphenylboron, tripropylammonium tetraphenylboron, trimethylammonium tetra(p-tolyl) boron, trimethylammonium tetra(o,p-dimethylphenyl) boron, tributylammonium tetra(p-trifluoromethylphenyl) boron, trimethylammonium tetra(p-trifluoromethylphenyl) boron, tributylammonium tetrapentafluorophenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, dimethylanilinium tetrakis(pentafluorophenyl) borate, triethylammonium tetraphenyl aluminum, tributylammonium tetraphenyl aluminum, trimethylammonium tetraphenyl aluminum, tripropylammonium tetraphenyl aluminum, trimethylammonium tetra(p-tolyl) aluminum, tripropylammonium tetra(p-tolyl) aluminum, triethylammonium tetra(o,p-dimethylphenyl) aluminum, tributylammonium tetra(p-trifluoromethylphenyl) aluminum, trimethylammonium tetra(p-trifluoromethylphenyl) aluminum, tributylammonium tetrapentafluorophenyl aluminum, N,N-diethylanilinium tetraphenyl aluminum, N,N-diethylanilinium tetrapentafluorophenyl aluminum, diethylammonium tetrapentatetraphenyl aluminum, triphenylphosphonium tetraphenyl aluminum, trimethylphosphonium tetraphenyl aluminum, tripropylammonium tetra(p-tolyl) boron, triethylammoniumtetra(o,p-dimethylphenyl) boron, triphenylcarbonium tetra(p-trifluoromethylphenyl) boron, triphenylcarbonium tetrapentafluorophenylboron, etc.

Specifically, aluminoxane may be used, and more specifically, methylaluminoxane (MAO) which is an alkylaluminoxane may be used.

As the first method, the catalyst composition may be prepared using a method including the following steps: 1) contacting the transition metal compound represented by Formula 2 with the compound represented by Formula 10 or 11 to obtain a mixture; and 2) adding the compound represented by Formula 12 to the mixture.

Further, as the second method, the catalyst composition may be prepared using a method of contacting the transition metal compound represented by Formula 2 with the compound represented by Formula 10.

In the first method among the methods of preparing the catalyst composition, the molar ratio of the transition metal compound represented by Formula 2/the compound represented by Formula 10 or 11 may preferably be $1/5,000$ to $1/2$, may more preferably be $1/1,000$ to $1/10$, and more specifically $1/500$ to $1/20$. When the molar ratio of the transition metal compound represented by Formula 2/the compound represented by Formula 10 or 11 exceeds $1/2$, the amount of an alkylating agent is very small, and the alkylation of a metal compound may not be completely carried out, and when the molar ratio is less than $1/5,000$, the activation of the alkylated metal compound may not be completely carried out due to the side reaction of the remaining excessive alkylating agent with the activation agent which is the compound of Formula 12 even though the alkylation of the metal compound may be carried out. Further, the molar ratio of the transition metal compound represented by Formula 2/the compound represented by Formula 12 may preferably be $1/25$ to 1, may more preferably be $1/10$ to 1, and more specifically $1/5$ to 1. When the molar ratio of the transition metal compound represented by Formula 2/the compound represented by Formula 12 exceeds 1, the amount of the activation agent is relatively small, and the activation of the metal compound may not be completely carried out, thereby deteriorating the activity of the catalyst composition prepared. When the molar ratio is less than $1/25$, the remaining excessive amount of the activation agent may decrease the economic performance in terms of the unit price of the catalyst composition, or the purity of a polymer thus produced may be decreased even though the activation of the metal compound may be completely carried out.

In the second method among the methods of preparing the catalyst composition, the molar ratio of the transition metal compound represented by Formula 2/the compound represented by Formula 10 may preferably be $1/10,000$ to $1/10$, may more preferably be $1/5,000$ to $1/100$, and more specifically $1/3,000$ to $1/500$. When the molar ratio exceeds $1/10$, the amount of the activation agent is relatively small, and the activation of the metal compound may not be completely carried out, thereby deteriorating the activity of the catalyst composition prepared. When the molar ratio is less than $1/10,000$, the remaining excessive amount of the activation agent may decrease the economic performance in terms of the unit price of the catalyst composition, or the purity of a polymer thus produced may be decreased even though the activation of the metal compound may be completely carried out.

Further, in an example of the present invention, when the transition metal compound according to the present invention is used as a catalyst for the polymerization reaction, it may be used as a catalyst for the polymerization reaction in the form of a composition further including a chain shuttling agent.

The chain shuttling agent refers to a compound allowing an exchange of polymeric chains (i.e., polymer chains or fragments) between two or more active catalyst sites of two olefin polymerization catalysts under olefin polymerization conditions, and the two olefin polymerization catalysts may be the transition metal compounds of the present invention. That is, the transfer of the polymer fragments occurs in one or more of the active sites of the transition metal compound.

Examples of the chain shuttling agent include trialkyl aluminum and dialkyl zinc compounds, especially triethyl aluminum, tri(i-propyl) aluminum, tri(i-butyl) aluminum, tri(n-hexyl) aluminum, tri(n-octyl) aluminum, triethyl gallium or diethyl zinc, and organometallic compounds, specifically tri(($C_1$-$C_8$)alkyl) aluminum or di(($C_1$-$C_8$)alkyl) zinc compounds, especially triethyl aluminum, tri(i-propyl) aluminum, tri(i-butyl) aluminum, tri(n-hexyl) aluminum, tri(n-octyl) aluminum, or a reaction product or mixture formed by a combination of diethyl zinc and a primary or secondary amine, a primary or secondary phosphine, a thiol, or a hydroxyl compound, especially bis (trimethylsilyl) amine, t-butyl (dimethyl) silanol, 2-hydroxymethylpyridine, di(n-pentyl) amine, 2,6-di(t-butyl) phenol, ethyl (1-naphthyl) amine, bis(2,3,6,7-dibenzo-1-azacycloheptanamine), diphenylphosphine, 2,6-di(t-butyl) thiophenol or 2,6-diphenylphenol in an amount less than a stoichiometric amount (with respect to number of hydrocarbyl groups). Preferably, a sufficient amine, phosphine, thiol or hydroxyl reagent is used such that at least one hydrocarbyl group per metal atom remains. The main reaction product of the most preferable combination for use in the present invention as a shuttling agent includes n-octyl aluminum di(bis(trimethylsilyl) amide), i-propyl aluminum bis(dimethyl(t-butyl) siloxide), and n-octyl aluminum di(pyridinyl-2-methoxide), i-butyl aluminum bis(dimethyl(t-butyl) siloxane), i-butyl aluminum di(bis(trimethylsilyl) amide), n-octyl aluminum di(pyridine-2-methoxide), i-butyl aluminum bis(di(n-pentyl) amide), n-octyl aluminum bis(2,6-di-t-butylphenoxide), n-octyl aluminum di(ethyl(1-naphthyl) amide), ethyl aluminum bis(t-butyl dimethyl siloxide), ethyl aluminum di(bis(trimethylsilyl) amide), ethyl aluminum bis(2,3,6,7-dibenzo-1-azacycloheptanamide), n-octyl aluminum bis(2,3,6,7-dibenzo-1-azacycloheptanamide), n-octyl aluminum bis (dimethyl (t-butyl) siloxide, ethyl zinc (2,6-diphenylphenoxide), and ethyl zinc (t-butoxide).

Hydrocarbon-based solvents such as pentane, hexane, heptane and the like, or aromatic solvents such as benzene, toluene and the like may be used as the reaction solvent in the preparation of the catalyst composition.

Further, the catalyst composition may include the transition metal compound and a cocatalyst compound in the form of being supported on a carrier.

Specifically, the polymerization reaction for polymerizing an olefin-based monomer in the presence of a catalyst composition containing the transition metal compound may be carried out by a solution polymerization process, a slurry process or a gas phase process using a continuous-slurry polymerization reactor, a loop slurry reactor, a gas phase reactor or a solution reactor. Further, homopolymerization with one olefin monomer or copolymerization with two or more types of monomers may be performed.

The polymerization of the polyolefin may be carried out by reaction at a temperature of about 25 to about 500° C. and a pressure of about 1 to about 100 kgf/cm².

Specifically, the polymerization of the polyolefin may be carried out at a temperature of about 25 to about 500° C., specifically about 25 to 200° C., and more specifically about 50 to 100° C. Further, a reaction pressure may be about 1 to about 100 kgf/cm², specifically about 1 to about 50 kgf/cm², and more specifically about 5 to about 40 kgf/cm².

Further, examples of olefinic monomers polymerizable using the transition metal compound and cocatalyst according to an embodiment of the present invention include ethylene, alpha-olefins, cyclic olefins and the like, and diene olefin-based monomers or triene olefin-based monomers having two or more double bonds may also be polymerized.

In the polyolefin prepared according to the present invention, specific examples of the olefin-based monomer include ethylene, propylene, 1-butene, 1-pentene, 4-methyl-1-pentene, 1-hexene, 1-heptene, 1-octene, 1-decene, 1-undecene, 1-dodecene, 1-tetradecene, 1-hexadecene, 1-eicosene and the like, or a copolymer obtained by copolymerizing two or more thereof.

The polyolefin may be, but is not limited to, a propylene polymer.

The polymer may be either a homopolymer or a copolymer. When the olefin polymer is a copolymer of ethylene and another comonomer, the monomer forming the copolymer is preferably ethylene, and at least one comonomer selected from the group consisting of propylene, 1-butene, 1-hexene, and 4-methyl-1-pentene and 1-octene.

MODES OF THE INVENTION

Hereinafter, preferred examples are provided to allow for a clearer understanding of the present invention. However, the following examples are merely presented to exemplify the present invention, and the scope of the present invention is not limited thereto.

Synthesis of Ligand and Transition Metal Compound

Organic reagents and solvents were purchased from Aldrich and Merck, and purified by a standard method and used. In all synthetic steps, the contact of the air and moisture were blocked to improve the reproducibility of experiments. Spectrums and images were obtained by using 500 MHZ nuclear magnetic resonance (NMR) for the identification of the structure of the compound.

EXAMPLES

Example 1: Synthesis of Ligand Compound a) Preparation of 8-(4,4,5,5-tetramethyl-1,3,2-dioxaborolan-2-yl)-1,2,3,4-tetrahydroquinoline

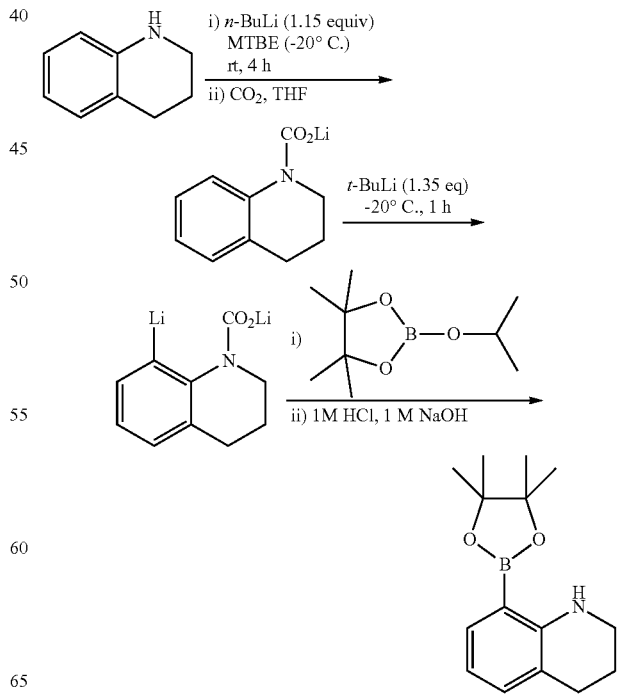

THQ (6 g, 45.05 mmol, 1 eq) was added to a Schlenk flask and vacuum-dried, hexane (150 mL, 0.3 M) was added thereto, and n-BuLi (19.82 mL, 49.56 mmol, 1.1 eq, 2.5 M in hexane) was added thereto at −20° C. The mixture was reacted overnight at room temperature and filtered to obtain a lithium compound. Diethyl ether (53.9 mL, 0.4 M) was added to the lithium compound (3 g, 21.56 mmol, 1 eq) thus obtained and bubbled with $CO_2$ at −78° C. After the mixture was left at room temperature overnight, THF (1.1 eq, 1.71 g, 23.72 mmol) was added at −20° C. t-BuLi (13.95 mL, 23.72 mmol, 1.1 eq, 1.7 M) was added thereto and reacted at −20° C. for 2 hours, and then 2-isopropyl-4,4,5,5-tetramethyl-1,3,2-dioxaborolane (10.03 g, 53.9 mmol, 2.5 eq) was added at −78° C. The temperature was gradually raised to room temperature, and a 1M HCl aqueous solution and EA were added at 0° C. after the reaction was complete. An organic layer was washed with 1 M NaOH and 1M $NaHCO_3$, and dehydrated with $MgSO_4$. 1.4 g of a yellow oily product was obtained in a yield of 25%.

$^1$H-NMR ($CDCl_3$): 7.42 (d, 1H), 6.97 (d, 1H), 6.48 (t, 1H), 5.70 (s, 1H), 3.34 (m, 2H), 2.73 (t, 2H), 1.90 (m, 2H), 1.31 (s, 12H)

b) Preparation of N-(2,6-diisopropylphenyl)-1-(6-bromopyridin-2-yl) Methanimine p-toluenesulfonic acid (3 drops) and a molecular sieve (1 g) were added to 2-formyl-6-bromopyridine (9.22 g, 49.57 mmol, 1 eq), and then toluene (100 mL) was added thereto. 2,6-diisopropylaniline (9.66 g, 54.52 mmol, 1.1 eq) was added thereto, stirred at 70° C. for 12 hours, and then cooled to room temperature. The molecular sieve was filtered, the solvent was removed and vacuum-drying was performed to produce a solid. MeOH was added at 50° C. under heating and then cooled to room temperature to obtain a solid. The resulting product was firstly filtered to obtain a solid, and then secondarily recrystallized in a refrigerator to obtain a secondary solid. Accordingly, 15.5 g of a solid was obtained in a yield of 90.5%.

c) Preparation of N-(2,6-diisopropylphenyl)-1-(6-(1,2,3,4-tetrahydroquinolin-8-yl) pyridin-2-yl) Methanimine

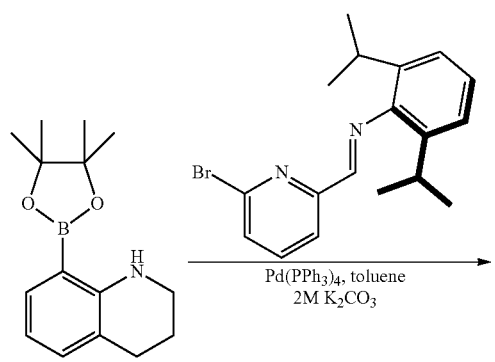

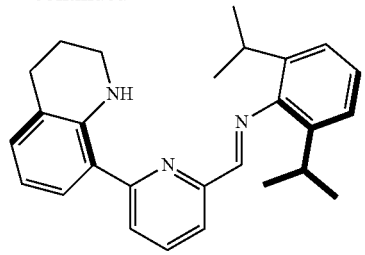

The N-(2,6-diisopropylphenyl)-1-(6-bromopyridin-2-yl) methanimine (1.799 g, 5.209 mmol, 1 eq) prepared as above was added to toluene (8 mL) and stirred. Meanwhile, separately, $Na_2CO_3$ (1.380 g, 13.0225 mmol, 2.5 eq) and tetrahydroquinoline-borolane (THQ-borolane) (1.350 g, 5.209 mmol, 1 eq) were added to a solvent including $H_2O$ (1.6 mL) and EtOH (1.6 mL) in a ratio of 1:1 and stirred.

A Br-imine toluene solution was transferred to the solution of $Na_2CO_3$ and THQ-borolane, followed by the addition of $Pd(PPh_3)_4$ (0.018 g, 0.0156 mmol, 0.3 mol % Pd). The mixture was stirred at 70° C. for 4 hours and cooled to room temperature. An organic layer was extracted with toluene/brine and dehydrated with $Na_2SO_4$ (product: 0.98 g, yield: 47%).

$^1$H-NMR (toluene_d8): 8.88 (s, 1H), 8.38 (s, 1H), 7.92 (d, 1H), 7.33 (d, 2H), 7.20 (t, 1H), 7.18 (t, 2H), 6.91 (d, 1H), 6.63 (t, 1H), 3.20 (m, 4H), 2.62 (m, 2H), 1.63 (m, 2H), 1.20 (d, 12H)

d) Preparation of (2,6-diisopropylphenyl)-N-(phenyl (6-(1,2,3,4-tetrahydroquinolin-8-yl)pyridin-2-yl) methyl) Aniline

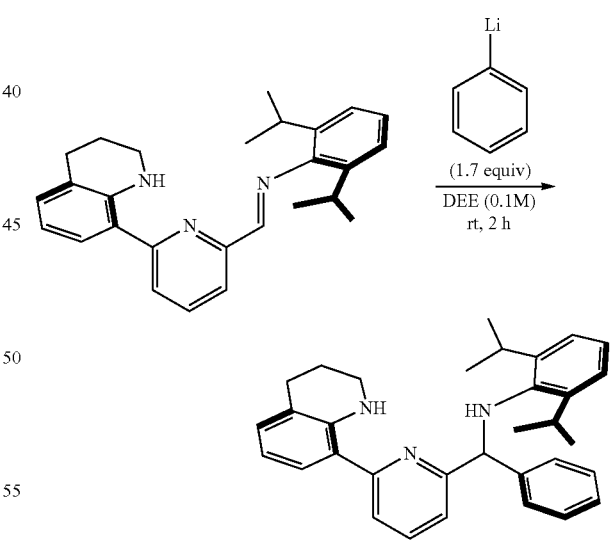

N-(2,6-diisopropylphenyl)-1-(6-(1,2,3,4-tetrahydroquinolin-8-yl)pyridin-2-yl) methanimine (0.95 g, 2.39 mmol, 1 eq) prepared as above was dissolved in diethyl ether (23.9 mL), the temperature was lowered to −78° C., and then phenyllithium (3.583 mL, 6.45 mmol, 2.7 eq, 1.8 M in DBE) was added thereto. When the reaction was complete, the mixture was quenched with 1 N $NH_4Cl$ and worked up with diethyl ether and water. Accordingly, 1.2 g (quantitative yield) of an orange solid was obtained.

¹H-NMR (toluene_d8): 8.01 (s, 1H), 7.41 (d, 2H), 7.31 (d, 1H), 7.15 (m, 4H), 7.06 (m, 3H), 6.86 (d, 2H), 6.73 (t, 1H), 6.61 (t, 1H), 5.24 (d, 1H), 4.32 (d, 1H), 3.05 (m, 2H), 3.0 (m, 2H), 2.52 (m, 2H), 1.52 (m, 2H), 1.01 (m, 12H)

Example 1-1: Synthesis of Transition Metal Compound (Formula 2a)

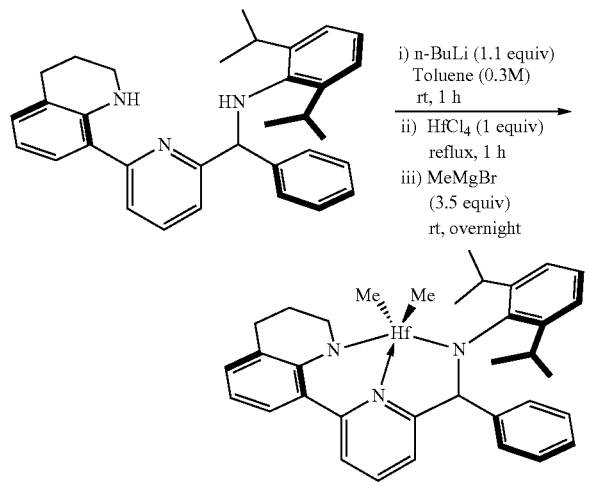

2,6-diisopropylphenyl-N-(phenyl(6-(1,2,3,4-tetrahydroquinolin-8-yl)pyridin-2-yl) methyl) aniline (0.8 g, 1.682 mmol, 1 eq) prepared in d) of Example 1 was added to toluene (5.607 mL, 0.3 M) and stirred, and then n-BuLi (1.413 mL, 3.532 mmol, 2.1 eq) was added dropwise thereinto. HfCl₄ (0.566 g, 1.766 mmol, 1.0 eq) was added and the mixture was heated at 90 to 100° C. for 2 hours. After the reaction was complete, the reaction mixture was cooled to room temperature, and MeMgBr (1.962 mL, 5.887 mmol, 3.5 eq, 3.0 M in DEE) was added, and the mixture was allowed to react at room temperature overnight. The solvent was vacuum-dried and then filtered. 588 mg of a yellow solid was obtained in a yield of 51.2%.

¹H-NMR (toluene_d8): 7.29 (d, 1H), 7.20 (d, 1H), 7.12 (m, 1H), 7.11 (m, 2H), 7.05 (m, 6H), 6.89 (t, 1H), 6.67 (t, 1H), 6.51 (d, 1H), 5.93 (s, 1H), 4.38 (d, 1H), 3.89 (t, 1H), 3.49 (t, 1H), 3.11 (m, 1H), 2.86 (m, 1H), 2.63 (m, 1H), 1.95 (m, 2H), 1.43 (d, 3H), 1.23 (d, 3H), 1.01 (d, 3H), 0.56 (s, 3H), 0.46 (d, 3H), 0.00 (s, 3H)

Example 1-2: Synthesis of Transition Metal Compound (Formula 2b)

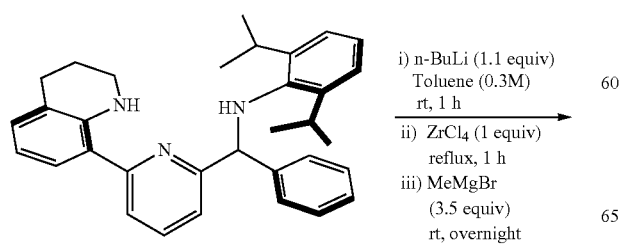

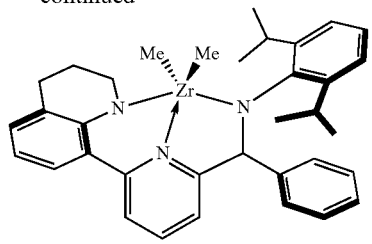

2,6-diisopropylphenyl-N-(phenyl(6-(1,2,3,4-tetrahydroquinolin-8-yl)pyridin-2-yl) methyl) aniline (0.82 g, 1.724 mmol, 1 eq) prepared in d) of Example 1 was added to toluene (5.747 mL, 0.3 M) and stirred, and then n-BuLi (1.45 mL, 3.6204 mmol, 2.1 eq) was added dropwise thereinto. ZrCl₄ (0.422 g, 1.810 mmol, 1.05 eq) was added and the mixture was heated at 90 to 100° C. for 2 hours.

After the reaction was complete, the reaction mixture was cooled to room temperature and MeMgBr (2.011 mL, 6.034 mmol, 3.5 eq, 3.0M in DEE) was added and allowed to react at room temperature overnight. The solvent was vacuum-dried and then filtered. The celite-filtered filtrate was dried, hexane was added thereto, the mixture was stirred and vacuum-dried, pentane was further added thereto, and the mixture was stirred and vacuum-dried. When a solid was obtained, pentane was added thereto to precipitate a catalyst. 672 mg of an orange solid was obtained in a yield of 65.5%.

¹H-NMR (toluene_d8): 7.30 (d, 1H), 7.20 (d, 1H), 7.12 (m, 2H), 7.06 (m, 7H), 6.89 (t, 1H), 6.67 (t, 1H), 6.54 (d, 1H), 5.73 (s, 1H), 4.80 (d, 1H), 3.99 (m, 1H), 3.57 (t, 1H), 3.07 (m, 1H), 2.86 (m, 1H), 2.67 (m, 1H), 1.95 (m, 2H), 1.45 (d, 3H), 1.21 (d, 3H), 0.96 (d, 3H), 0.68 (s, 3H), 0.50 (d, 3H), 0.09 (s, 3H)

Example 2: Synthesis of Ligand Compound

Synthesis of 2,6-diisopropyl-N-((2-isopropylphenyl)(6-(1,2,3,4-tetrahydroquinolin-8-yl) pyridin-2-yl) methyl) Aniline

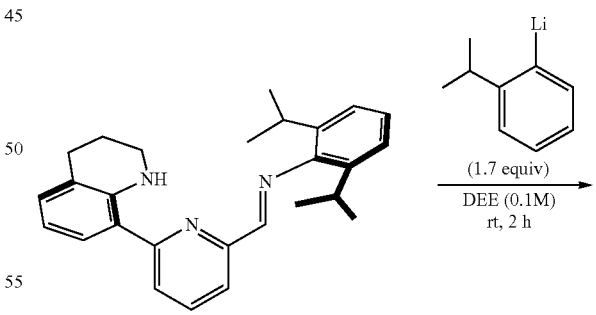

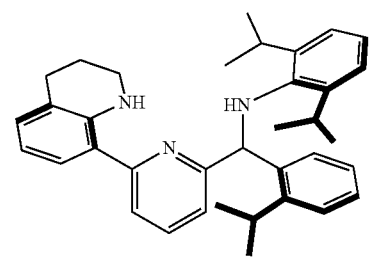

1-Br-2-isopropylbenzene (2.13 g, 10.67 mmol, 2.7 eq) was added to THF (21.38 mL) and t-BuLi (13.62 mL) was added at −78° C. The reaction was allowed to proceed for 2 hours and then the reaction product was warmed to room temperature.

Diethyl ether was added to N-(2,6-diisopropylphenyl)-1-(6-(1,2,3,4-tetrahydroquinolin-8-yl) pyridin-2-yl) methanimine, and cumene lithium was added dropwise at −78° C. After the temperature was raised to room temperature, the reaction was performed overnight, the reaction product was quenched with 1N NH$_4$Cl and ether/H$_2$O work-up was carried out. Dehydration was performed using Na$_2$SO$_4$ and the solvent was vacuum-dried with a rotavapor. 2.22 g of pure yellow oil was obtained in a quantitative yield.

$^1$H-NMR (toluene_d8): 7.97 (s, 1H), 7.66 (d, 1H), 7.30 (d, 1H), 7.14 (m, 8H), 6.83 (d, 1H), 6.56 (t, 1H), 5.61 (d, 1H), 4.04 (d, 1H), 2.9 (m, 5H), 2.5 (m, 2H), 1.51 (m, 2H), 1.01 (d, 12H), 1.00 (d, 3H), 0.97 (d, 3H)

Example 2-1: Synthesis of Transition Metal Compound (Formula 2c)

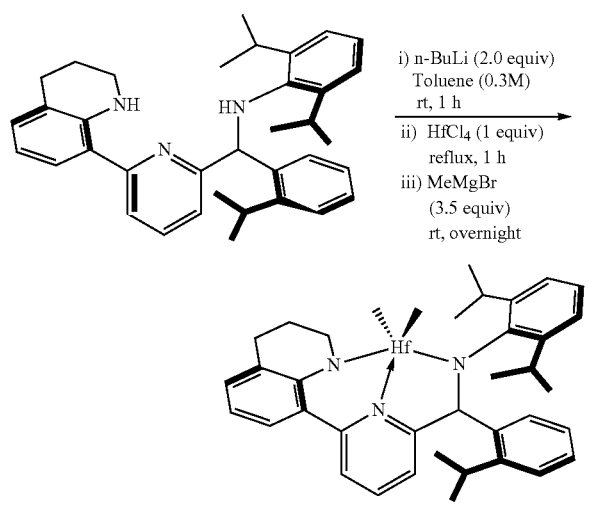

2,6-diisopropyl-N-((2-isopropylphenyl)(6-(1,2,3,4-tetrahydroquinolin-8-yl) pyridin-2-yl) methyl) aniline (1 g, 1.9314 mmol, 1 eq) obtained in Example 2 was added to toluene (6.433 mL, 0.3 M) and stirred, and n-BuLi (1.622 mL, 4.056 mmol, 2.1 eq) was added dropwise. HfCl$_4$ (0.619 g, 1.9314 mmol, 1.0 eq) was added and the mixture was heated at 90 to 100° C. for 2 hours. After the reaction was complete, the reaction mixture was cooled, MeMgBr (2.2533 mL, 6.76 mmol, 3.5 eq, 3.0 M in DEE) was added thereto, and the reaction was allowed to proceed overnight at room temperature. The solvent was vacuum-dried and then filtered. 680 mg of a yellow solid was obtained in a yield of 33%.

$^1$H-NMR (toluene_d8): 7.29 (m, 2H), 7.21 (d, 1H), 7.10 (m, 6H), 6.88 (t, 1H), 6.89 (t, 1H), 6.68 (t, 1H), 6.60 (d, 1H), 6.55 (s, 1H), 4.42 (d, 1H), 3.93 (m, 1H), 3.49 (t, 1H), 3.19 (m, 1H), 2.82 (m, 2H), 2.67 (m, 1H), 1.97 (m, 2H), 1.41 (d, 3H), 1.18 (m, 6H), 1.01 (d, 3H), 0.70 (d, 3H), 0.60 (s, 3H), 0.45 (d, 3H), 0.03 (s, 3H)

Example 2-2: Synthesis of Transition Metal Compound (Formula 2d)

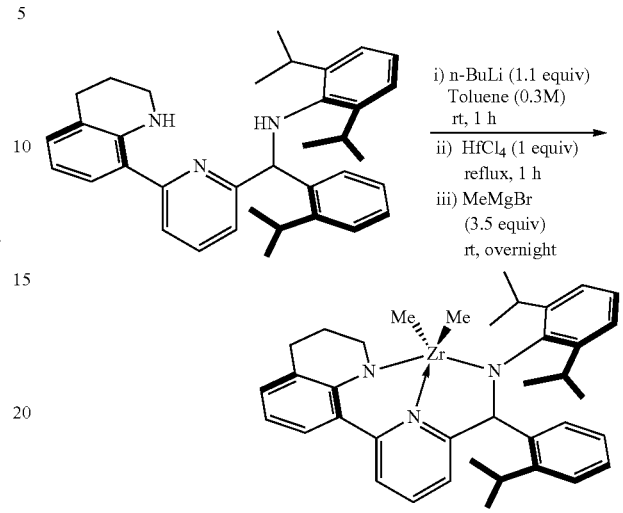

2,6-diisopropyl-N-((2-isopropylphenyl)(6-(1,2,3,4-tetrahydroquinolin-8-yl) pyridin-2-yl) methyl) aniline (1.32 g, 2.5494 mmol, 1 eq) obtained in Example 2 was added to toluene (8.5 mL, 0.3 M) and stirred, and n-BuLi (2.1415 mL, 5.354 mmol, 2.1 eq) was added dropwise. ZrCl$_4$ (0.594 g, 2.5494 mmol, 1.05 eq) was added and the mixture was heated at 90 to 100° C. for 2 hours.

After the reaction was complete, the reaction mixture was cooled, MeMgBr (2.974 mL, 8.923 mmol, 3.5 eq, 3.0 M in DEE) was added thereto, and the reaction was allowed to proceed overnight at room temperature. The solvent was vacuum-dried and then filtered. The celite-filtered filtrate was dried, hexane was added thereto, the mixture was stirred and vacuum-dried, pentane was further added thereto, and the mixture was stirred and vacuum-dried. When a solid was obtained, pentane was added thereto to precipitate a catalyst. 310 mg of an orange solid was obtained in a yield of 20%.

$^1$H-NMR (toluene_d8): 7.26 (m, 2H), 7.23 (d, 1H), 7.10 (m, 6H), 7.02 (m, 1H), 6.87 (t, 1H), 6.69 (t, 1H), 6.64 (d, 1H), 6.36 (s, 1H), 4.85 (d, 1H), 4.03 (m, 1H), 3.56 (t, 1H), 3.15 (m, 1H), 2.85 (m, 2H), 2.67 (m, 1H), 1.97 (m, 2H), 1.42 (d, 3H), 1.17 (m, 6H), 0.94 (d, 3H), 0.71 (m, 6H), 0.49 (d, 3H), 0.12 (d, 3H)

Example 3: Synthesis of Ligand Compound a) Synthesis of methyl-7-(4,4,5,5-tetramethyl-1,3,2-dioxaborolan-2-yl) Indolin

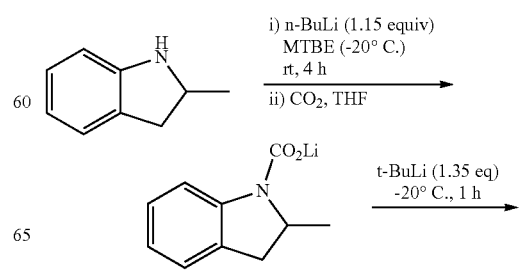

-continued

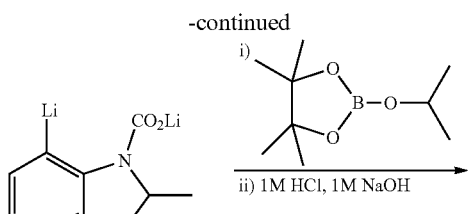

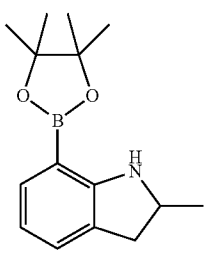

After 2-methylindoline (10 g, 75.08 mmol, 1 eq) was dissolved in hexane (250 mL, 0.3 M) followed by lithiation by adding n-BuLi (33.03 mL, 82.59 mol, 1.1 eq), the reaction was performed overnight, and the mixture was filtered to obtain a solid.

Diethyl ether (99.2 mL, 0.4 M) was added to the lithium compound (5.52 g, 39.675 mmol, 1 eq) thus obtained and bubbled with $CO_2$ at −78° C. The mixture was stirred at room temperature for 1 day, and THF (1.1 eq, 3.54 mL, 43.643 mmol, 1.1 eq) was added at −20° C.

t-BuLi (27.8 mL, 43.643 mmol, 1.1 eq, 1.57 M) was added thereto and reacted at −20° C. for 2 hours, and then 2-isopropyl-4,4,5,5-tetramethyl-1,3,2-dioxaborolane (20.24 g, 99.19 mmol, 2.5 eq) was added at −78° C. The temperature was gradually raised to room temperature, and a 1M HCl aqueous solution and EA were added at 0° C. after the reaction was complete. An organic layer was washed with 1 M NaOH and 1M $NaHCO_3$, and dehydrated with $MgSO_4$. Accordingly, 3.1 g of a beige solid was obtained in a yield of 30%.

$^1$H-NMR ($CDCl_3$): 7.36 (d, 1H), 7.08 (d, 1H), 6.58 (t, 1H), 4.93 (s, 1H), 4.01 (m, 1H), 3.07 (m, 1H), 2.60 (m, 1H), 1.31 (s, 12H), 1.25 (s, 3H)

b) Preparation of N-(2,6-diisopropylphenyl)-1-(6-(2-methylindolin-7-yl) pyridin-2-yl) Methanimine

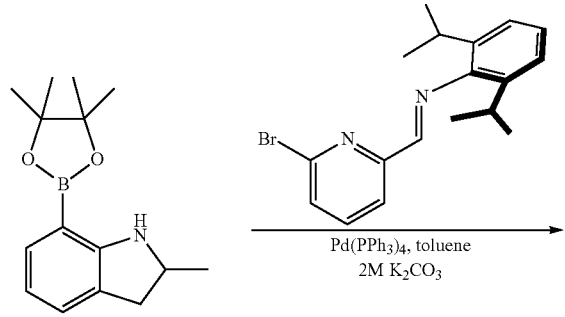

-continued

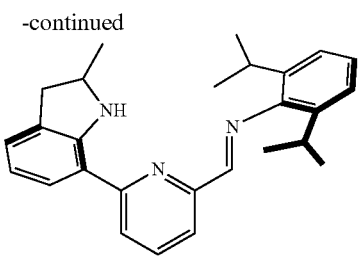

N-(2,6-diisopropylphenyl)-1-(6-bromopyridin-2-yl) methanimine (3 g, 8.69 mmol, 1 eq) prepared as above was added to toluene (13.33 mL) and stirred. Meanwhile, separately, $Na_2CO_3$ (2.303 g, 21.725 mmol, 2.5 eq) and 2 M 2-methyl-7-(4,4,5,5-tetramethyl-1,3,2-dioxaborolan-2-yl) indolin (I-borolane) (2.25 g, 8.69 mmol, 1 eq) were added to a solvent including $H_2O$ (2.66 mL) and EtOH (2.66 mL) in a ratio of 1:1 and stirred.

A Br-imine toluene solution was transferred to the solution of I-borolane, followed by the addition of $Pd(PPh_3)_4$ (0.0301 g, 0.026 mmol, 0.3 mol % Pd). The mixture was stirred at 70° C. for 4 hours and cooled to room temperature. An organic layer was extracted with toluene/brine and dehydrated with $Na_2SO_4$. 1.78 g of the product was obtained in a yield of 52%.

$^1$H-NMR (toluene_d8): 8.38 (s, 1H), 7.86 (d, 1H), 7.66 (s, 1H), 7.38 (d, 2H), 7.19 (t, 1H), 7.13 (m, 3H), 6.68 (t, 1H), 3.89 (m, 1H), 3.15 (m, 2H), 2.89 (m, 1H), 2.40 (m, 1H), 1.18 (m, 12H), 1.1 (m, 3H)

c) Preparation of 2,6-diisopropyl-N-((6-(2-methylindolin-7-yl) pyridin-2-yl) (phenyl) methyl) Aniline

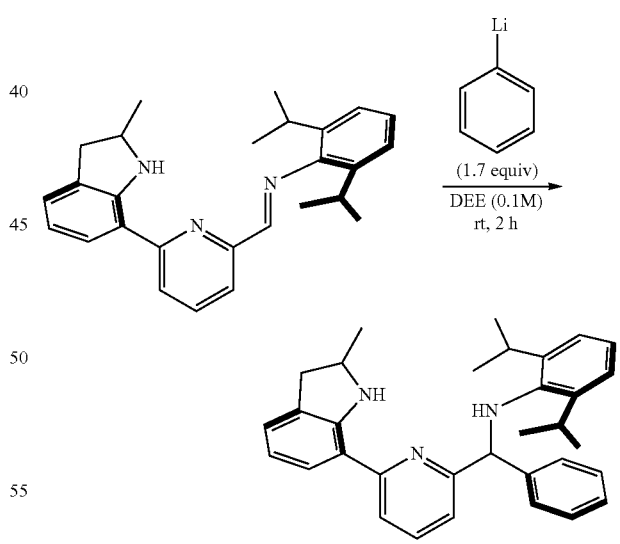

In order to attach a phenyl to a ligand precursor, the synthesized ligand precursor (750 mg, 1.886 mmol, 1 eq) was dissolved in diethyl ether (18.86 mL) and the temperature was lowered to −78° C. Then, phenyl lithium (2.83 mL, 5.093 mmol, 2.7 eq, 1.8 M in DBE) was added. When the reaction was complete, the mixture was quenched with 1 N $NH_4Cl$ and worked up with diethyl ether and water. Accordingly, 880 mg (quantitative yield) of the ligand was obtained.

¹H-NMR (toluene_d8): 7.40 (m, 3H), 7.24 (d, 1H), 7.14 (m, 3H), 7.06 (m, 4H), 6.92 (m, 2H), 6.74 (d, 1H), 6.65 (m, 1H), 5.26 (m, 1H), 4.34 (m, 1H), 3.74 (m, 1H), 3.05 (m, 2H), 2.83 (m, 1H), 2.35 (m, 1H), 1.02 (m, 12H), 0.93 (m, 3H)

Example 3-1: Synthesis of Transition Metal Compound (Formula 2e)

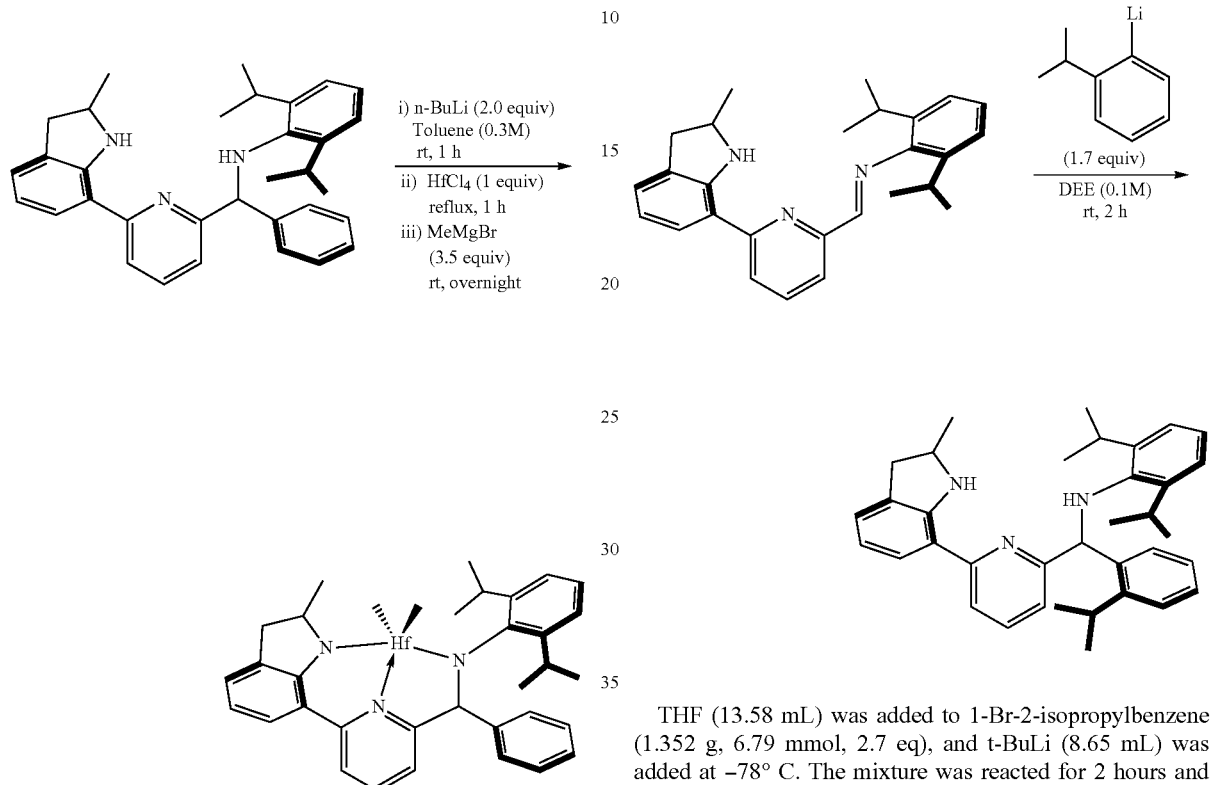

2,6-diisopropyl-N-((6-(2-methylindolin-7-yl) pyridin-2-yl) (phenyl) methyl) aniline (0.7 g, 1.4716 mmol, 1 eq) which was the ligand synthesized in d) of Example 3 was added to toluene (4.905 mL, 0.3 M) and stirred, and then n-BuLi (1.236 mL, 3.09 mmol, 2.1 eq) was added dropwise thereinto. HfCl₄ (0.495 g, 1.5452 mmol, 1.05 eq) was added and the mixture was heated at 90 to 100° C. for 2 hours. After the reaction was complete, the reaction mixture was cooled to room temperature and MeMgBr (1.72 mL, 5.1506 mmol, 3.5 eq, 3.0 M in DEE) was added and the mixture was allowed to react at room temperature overnight. The solvent was vacuum-dried and then filtered. The celite-filtered filtrate was dried, hexane was added thereto, the mixture was stirred and vacuum-dried, pentane was further added thereto, and the mixture was stirred and vacuum-dried. When a solid was obtained, pentane was added thereto to precipitate to obtain 492 mg of a yellow solid as a catalyst which is the title compound in a yield of 49%.

¹H-NMR (toluene_d8): 7.40 (d, 1H), 7.30 (d, 1H), 7.17 (d, 2H), 7.04 (m, 6H), 6.91 (t, 2H), 6.67 (t, 1H), 6.45 (d, 1H), 5.72 (s, 1H), 4.99 (m, 1H), 3.83 (m, 1H), 3.26 (m, 1H), 3.03 (m, 1H), 2.50 (d, 1H), 1.44 (d, 3H), 1.32 (d, 3H), 1.17 (d, 3H), 0.95 (d, 3H), 0.70 (s, 3H), 0.49 (d, 3H), 0.16 (s, 3H)

Example 4: Synthesis of Ligand Compound

Preparation of 2,6-diisopropyl-N-((2-isopropylphenyl)(6-(2-methylindolin-7-yl)pyridin-2-yl) methyl) Aniline

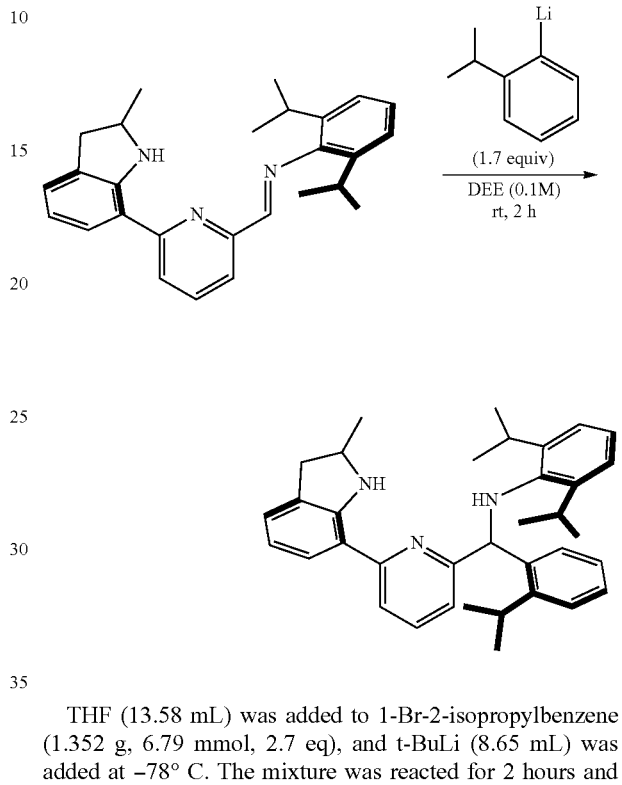

THF (13.58 mL) was added to 1-Br-2-isopropylbenzene (1.352 g, 6.79 mmol, 2.7 eq), and t-BuLi (8.65 mL) was added at −78° C. The mixture was reacted for 2 hours and the temperature was raised to room temperature. Diethyl ether (25.15 mL) was added to a ligand precursor (1 g, 2.515 mmol, 1 eq), and cumene lithium was added dropwise at −78° C. The temperature was raised to room temperature, the reaction was allowed to proceed overnight, the mixture was quenched with 1 N NH₄Cl, and then worked up with ether/H₂O. Dehydration was performed using Na₂SO₄ and the solvent was vacuum-dried using a rotavapor. 1.49 g of yellow oil was obtained in a quantitative yield.

¹H-NMR (toluene_d8): 7.75-5.60 (m, 15H), 4.08-2.30 (m, 7H), 1.13-1.02 (m, 21H)

Example 4-1: Synthesis of Transition Metal Compound (Formula 2g)

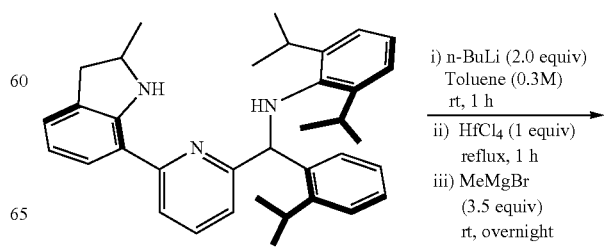

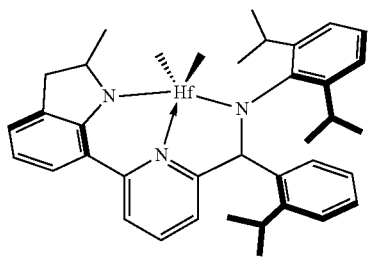

2,6-diisopropyl-N-((2-isopropylphenyl)(6-(2-methylindolin-7-yl)pyridin-2-yl) methyl) aniline (1.17 g, 2.26 mmol, 1 eq) which was the ligand synthesized in Example 4 was added to toluene (7.533 mL, 0.3 M) and stirred, and n-BuLi (1.898 mL, 4.745 mmol, 2.1 eq) was added dropwise. HfCl$_4$ (0.724 g, 2.26 mmol, 1.05 eq) was added and the mixture was heated at 90 to 100° C. for 2 hours. After the reaction was complete, the reaction mixture was cooled to room temperature and MeMgBr (2.637 mL, 7.91 mmol, 3.5 eq, 3.0 M in DEE) was added and allowed to react at room temperature overnight. The celite-filtered filtrate was dried, hexane was added thereto, the mixture was stirred and vacuum-dried, pentane was further added thereto, and the mixture was stirred and vacuum-dried. When a solid was obtained, pentane was added thereto to precipitate to obtain 400 mg of a yellow solid in a yield of 25%.

$^1$H-NMR (toluene_d8): 7.37 (d, 1H), 7.28 (d, 2H), 7.18 (d, 1H), 7.10 (m, 5H), 6.89 (t, 1H), 6.67 (t, 1H), 6.59 (d, 1H), 6.42 (s, 1H), 5.01 (m, 1H), 3.92 (m, 1H), 3.26 (m, 1H), 3.10 (m, 1H), 2.84 (m, 1H), 2.52 (d, 1H), 1.40 (d, 3H), 1.34 (d, 3H), 1.16 (dd, 6H), 0.95 (d, 3H), 0.74 (s, 3H), 0.68 (d, 3H), 0.45 (d, 3H), 0.20 (s, 3H)

Example 5: Synthesis of Ligand Compound a) Preparation of 2-methyl-8-(4,4,5,5-tetramethyl-1,3,2-dioxaborolan-2-yl)-1,2,3,4-tetrahydroquinoline

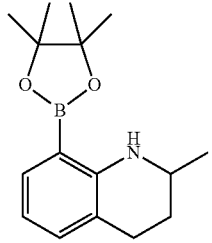

2-methyl-THQ (10 g, 67.925 mmol, 1 eq) was added to a Schlenk flask and vacuum-dried, hexane (226 mL, 0.3 M) was added thereto, and n-BuLi (29.89 mL, 74.718 mmol, 1.1 eq, 2.5 M in hexane) was added thereto at −20° C. The mixture was reacted overnight at room temperature and filtered to obtain a lithium compound. Diethyl ether (113.21 mL, 0.4 M) was added to the lithium compound (10.40 g, 67.925 mmol, 1 eq) thus obtained and bubbled with CO$_2$ at −78° C. After the mixture was left at room temperature overnight, THF (1.1 eq, 5.388 g, 74.72 mmol) was added at −20° C. t-BuLi (47.6 mL, 74.72 mmol, 1.1 eq, 1.7 M) was added thereto, and reacted at −20° C. for 2 hours, and then 2-isopropyl-4,4,5,5-tetramethyl-1,3,2-dioxaborolane (31.6 g, 169.8 mmol, 2.5 eq) was added at −78° C. The temperature was gradually raised to room temperature, and a 1M HCl aqueous solution and EA were added at 0° C. after the reaction was complete. An organic layer was washed with 1 M NaOH and 1M NaHCO$_3$, and dehydrated with MgSO$_4$. 9.9 g of a yellow oily product was obtained in a yield of 53.4%.

$^1$H-NMR (CDCl$_3$): 7.45 (d, 1H), 7.01 (d, 1H), 6.52 (t, 1H), 5.83 (s, 1H), 3.48 (m, 1H), 2.80 (m, 2H), 1.91 (m, 1H), 1.58 (m, 1H), 1.35 (s, 12H), 1.26 (s, 3H)

b) Preparation of N-(2,6-diisopropylphenyl)-1-(6-(2-methyl-1,2,3,4-tetrahydroquinolin-8-yl)pyridin-2-yl) Methanimine

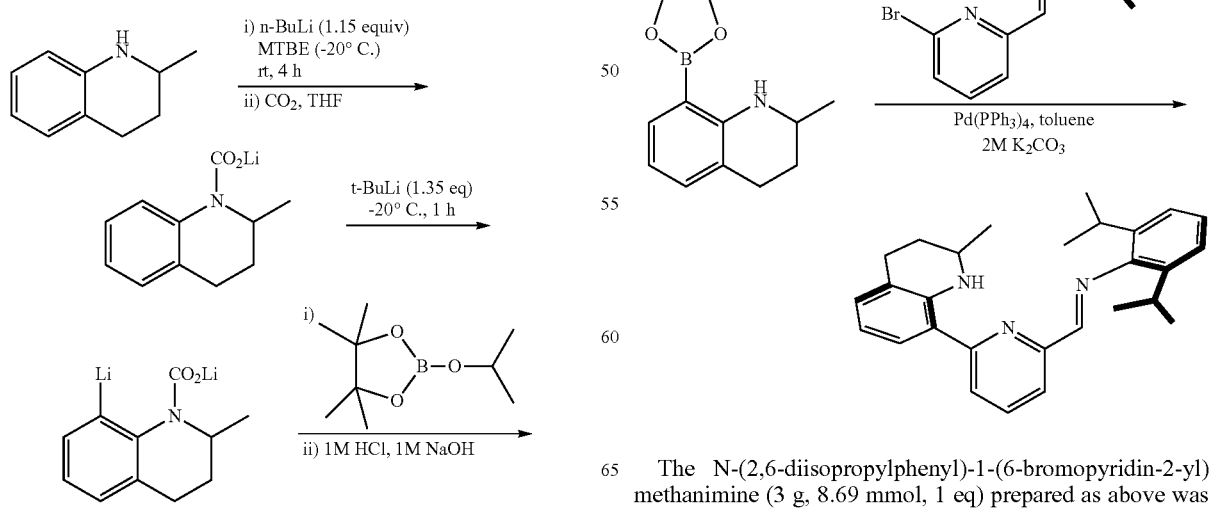

The N-(2,6-diisopropylphenyl)-1-(6-bromopyridin-2-yl) methanimine (3 g, 8.69 mmol, 1 eq) prepared as above was added to toluene (13.33 mL) and stirred. Meanwhile, separately, Na₂CO₃ (2.303 g, 21.725 mmol, 2.5 eq) and THQ-borolane (2.373 g, 8.69 mmol, 1 eq) were added to a solvent including H₂O (2.66 mL) and EtOH (2.66 mL) in a ratio of 1:1 and stirred.

A Br-imine toluene solution was transferred to the solution of THQ-borolane, followed by the addition of Pd(PPh₃)₄ (0.0301 g, 0.026 mmol, 0.3 mol % Pd). The mixture was stirred at 70° C. for 4 hours and cooled to room temperature. An organic layer was extracted with toluene/brine and dehydrated with Na₂SO₄. 3.08 g of a product was obtained in a yield of 86%.

¹H-NMR (toluene_d8): 8.96 (s, 1H), 8.41 (s, 1H), 7.92 (d, 1H), 7.33 (d, 2H), 7.19 (t, 1H), 7.13 (m, 3H), 6.94 (d, 1H), 6.64 (m, 1H), 3.30 (m, 1H), 3.16 (m, 2H), 2.72 (m, 1H), 2.61 (m, 1H), 1.56 (m, 1H), 1.36 (m, 1H), 1.19 (m, 12H), 1.05 (d, 3H)

c) Preparation of 2,6-diisopropyl-N-((6-(2-methyl-1,2,3,4-tetrahydroquinolin-8-yl)pyridin-2-yl)(phenyl) methyl) Aniline

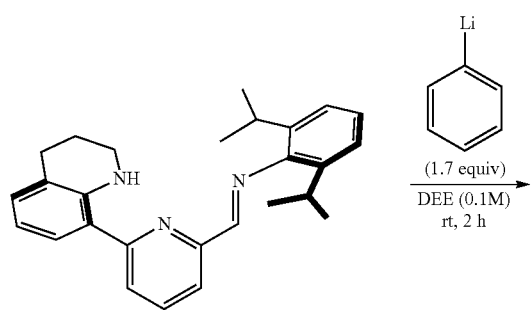

N-(2,6-diisopropylphenyl)-1-(6-(2-methyl-1,2,3,4-tetrahydroquinolin-8-yl)pyridin-2-yl) methanimine (1 g, 2.43 mmol, 1 eq) which was the synthesized ligand precursor was dissolved in diethyl ether (24.3 mL), the temperature was lowered to −78° C., and then phenyl lithium (3.645 mL, 6.561 mmol, 2.7 eq, 1.8 M in DBE) was added thereto. When the reaction was complete, the mixture was quenched with 1 N NH₄Cl and worked up with diethyl ether and water. Accordingly, 1.2 g (quantitative yield) of the product was obtained.

¹H-NMR (toluene_d8): 8.20 (s, 1H), 7.33-6.64 (m, 14H), 5.25 (m, 1H), 4.51 (m, 1H), 3.20 (m, 1H), 3.13 (m, 2H), 2.63 (m, 1H), 2.58 (m, 1H), 1.53 (m, 1H), 1.34 (m, 1H), 1.04 (m, 12H), 0.84 (m, 3H)

Example 5-1: Synthesis of Transition Metal Compound (Formula 2i)

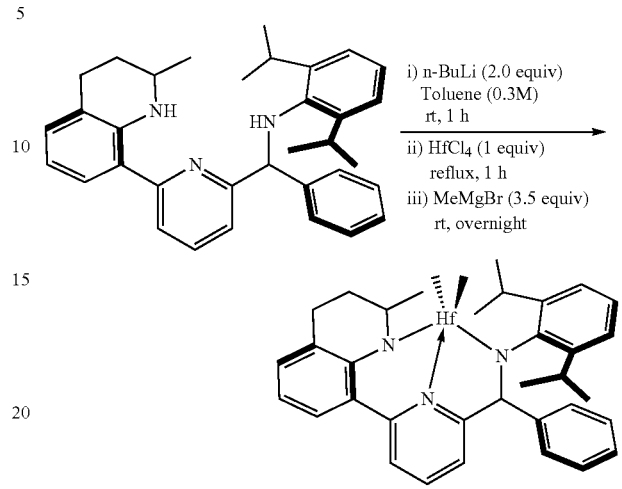

2,6-diisopropyl-N-((6-(2-methyl-1,2,3,4-tetrahydroquinolin-8-yl)pyridin-2-yl)(phenyl) methyl) aniline (0.8 g, 1.634 mmol, 1 eq) which was the ligand synthesized in c) of Example 5 was added to toluene (5.44 mL, 0.3 M) and stirred, and n-BuLi (1.3722 mL, 3.431 mmol, 2.1 eq) was added dropwise. HfCl₄ (0.549 g, 1.716 mmol, 1.05 eq) was added and the mixture was heated at 90 to 100° C. for 2 hours.

After the reaction was complete, the reaction mixture was cooled and MeMgBr (1.906 mL, 5.719 mmol, 3.5 eq, 3.0 M in DEE) was added and allowed to react at room temperature overnight. The solvent was vacuum-dried and filtered. The celite-filtered filtrate was dried, hexane was added thereto, the mixture was stirred and vacuum-dried, pentane was further added thereto, and the mixture was stirred and vacuum-dried. When a solid was obtained, pentane was added thereto to precipitate to obtain 430 mg of a yellow solid catalyst in a yield of 41%.

¹H-NMR (toluene_d8): 7.31 (d, 1H), 7.20 (d, 1H), 7.10 (m, 9H), 6.89 (t, 1H), 6.68 (t, 1H), 6.52 (d, 1H), 5.90 (s, 1H), 4.80 (s, 1H), 3.90 (m, 1H), 3.04 (m, 2H), 2.61 (m, 1H), 2.19 (m, 1H), 1.80 (m, 1H), 1.45 (d, 3H), 1.30 (d, 3H), 1.18 (d, 3H), 0.95 (d, 3H), 0.62 (s, 3H), 0.50 (d, 3H), −0.02 (s, 3H)

Example 6: Synthesis of Ligand Compound

Preparation of 2,6-diisopropyl-N-((2-isopropylphenyl)(6-(2-methyl-1,2,3,4-tetrahydroquinolin-8-yl) pyridin-2-yl) methyl) Aniline

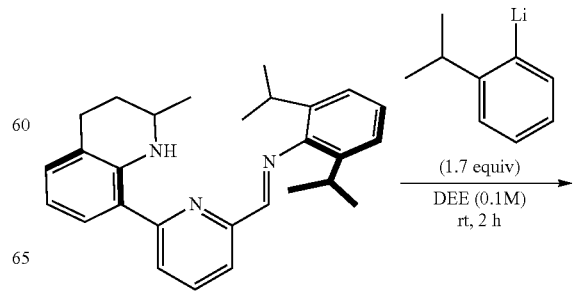

-continued

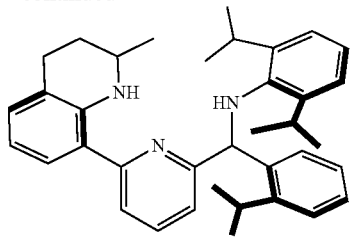

THF (13.122 mL) was added to 1-Br-2-isopropylbenzene (1.306 g, 6.561 mmol, 2.7 eq), and t-BuLi (8.36 mL) was added at −78° C. The mixture was reacted for 2 hours and the temperature was raised to room temperature to prepare cumene lithium. Diethyl ether (24.3 mL) was added to N-(2,6-diisopropylphenyl)-1-(6-(2-methyl-1,2,3,4-tetrahydroquinolin-8-yl)pyridin-2-yl) methanimine (1 g, 2.43 mmol, 1 eq) which was the ligand precursor prepared in b) of Example 5, and the cumene lithium was added dropwise at −78° C. The temperature was raised to room temperature, the reaction was allowed to proceed overnight, the mixture was quenched with 1 N NH$_4$Cl, and then worked up with ether/H$_2$O. Dehydration was performed using Na$_2$SO$_4$ and the solvent was vacuum-dried using a rotavapor. 1.48 g of yellow oil was obtained in a quantitative yield.

$^1$H-NMR (toluene_d8): 8.30-5.60 (m, 15H), 4.73-2.59 (m, 10H), 1.14-0.84 (m, 21H)

Example 6-1: Synthesis of Transition Metal Compound (Formula 2k)

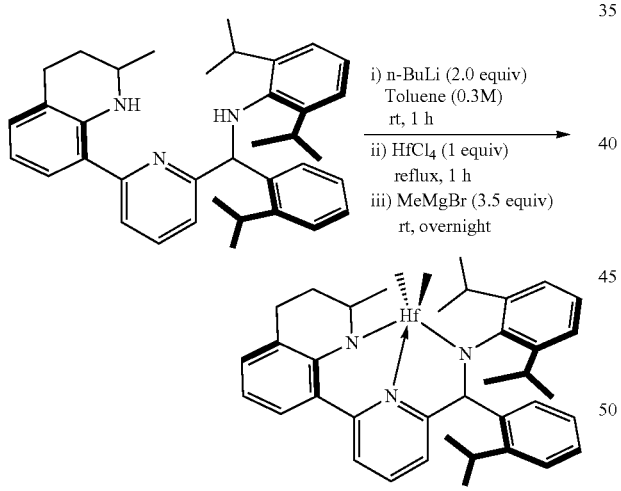

2,6-diisopropyl-N-((2-isopropylphenyl)(6-(2-methyl-1,2,3,4-tetrahydroquinolin-8-yl) pyridin-2-yl) methyl) aniline (1.21 g, 2.27 mmol, 1 eq) which was the ligand prepared in Example 6 was added to toluene (7.567 mL, 0.3 M) and stirred, and n-BuLi (1.907 mL, 4.767 mmol, 2.1 eq) was added dropwise. HfCl$_4$ (0.7634 g, 2.3835 mmol, 1.05 eq) was added and the mixture was heated at 90 to 100° C. for 2 hours. After the reaction was complete, the reaction mixture was cooled and MeMgBr (2.65 mL, 7.945 mmol, 3.5 eq, 3.0 M in DEE) was added and allowed to react at room temperature overnight. The solvent was vacuum-dried and filtered. The celite-filtered filtrate was dried, hexane was added thereto, the mixture was stirred and vacuum-dried, pentane was further added thereto, and the mixture was stirred and vacuum-dried. When a solid was obtained, pentane was added thereto to precipitate to obtain 320 mg of a yellow solid catalyst in a yield of 19%.

$^1$H-NMR (toluene_d8): 7.34 (d, 1H), 7.32 (d, 1H), 7.20 (d, 1H), 7.12 (m, 3H), 7.10 (m, 1H), 7.07 (m, 3H), 6.86 (t, 1H), 6.69 (t, 1H), 6.60 (d, 1H), 6.523 (s, 1H), 4.82 (m, 1H), 3.95 (m, 1H), 3.10 (m, 1H), 3.01 (m, 1H), 2.79 (m, 1H), 2.63 (m, 1H), 2.20 (m, 1H), 1.83 (m, 1H), 1.42 (d, 3H), 1.31 (d, 3H), 1.13 (m, 6H), 0.93 (d, 3H), 0.71 (d, 3H), 0.65 (s, 3H), 0.48 (d, 3H), 0.01 (s, 3H)

Example 7: Synthesis of Ligand Compound

Preparation of N-([1,1'-biphenyl]-2-yl(6-((S)-2-methyl-1,2,3,4-tetrahydroquinolin-8-yl)pyridin-2-yl) methyl)-2,6-diisopropyl Aniline

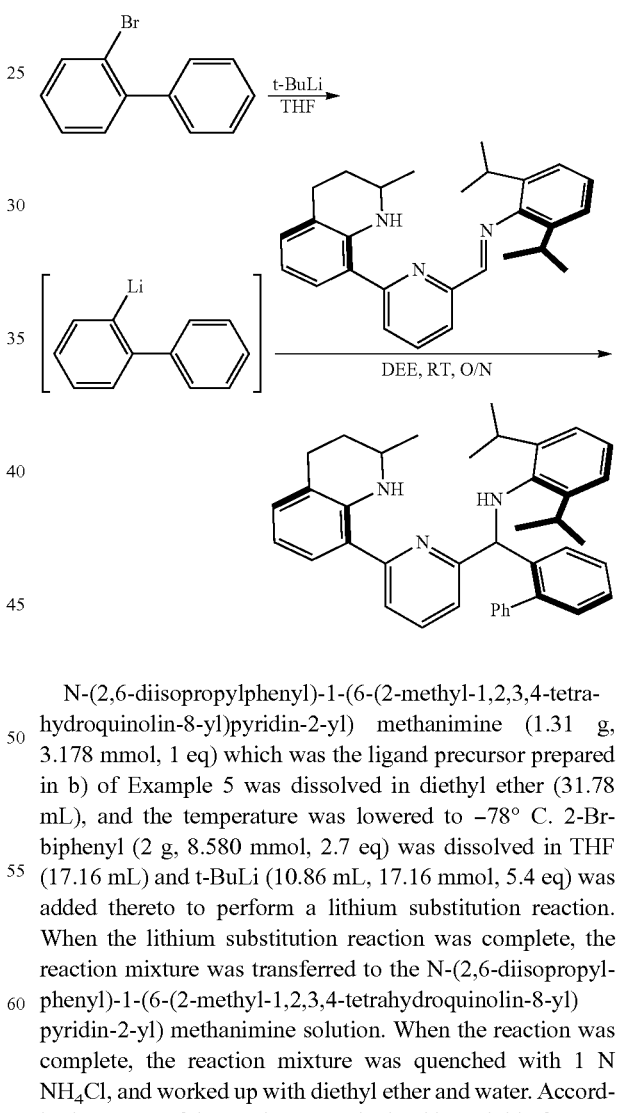

N-(2,6-diisopropylphenyl)-1-(6-(2-methyl-1,2,3,4-tetrahydroquinolin-8-yl)pyridin-2-yl) methanimine (1.31 g, 3.178 mmol, 1 eq) which was the ligand precursor prepared in b) of Example 5 was dissolved in diethyl ether (31.78 mL), and the temperature was lowered to −78° C. 2-Br-biphenyl (2 g, 8.580 mmol, 2.7 eq) was dissolved in THF (17.16 mL) and t-BuLi (10.86 mL, 17.16 mmol, 5.4 eq) was added thereto to perform a lithium substitution reaction. When the lithium substitution reaction was complete, the reaction mixture was transferred to the N-(2,6-diisopropylphenyl)-1-(6-(2-methyl-1,2,3,4-tetrahydroquinolin-8-yl) pyridin-2-yl) methanimine solution. When the reaction was complete, the reaction mixture was quenched with 1 N NH$_4$Cl, and worked up with diethyl ether and water. Accordingly, 2.38 g of the product was obtained in a yield of 100%.

$^1$H-NMR (toluene_d8): 8.50-6.64 (m, 18H), 5.50-1.48 (m, 9H), 0.9 (m, 15H)

Example 7-1: Synthesis of Transition Metal Compound (Formula 2m)

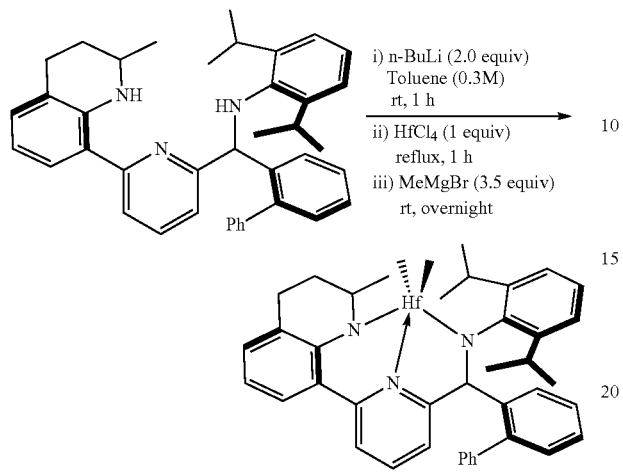

N-([1,1'-biphenyl]-2-yl(6-((S)-2-methyl-1,2,3,4-tetrahydroquinolin-8-yl)pyridin-2-yl) methyl)-2,6-diisopropyl aniline (2.38 g, 4.2064 mmol, 1 eq) prepared in Example 7 was added to toluene (14.02 mL, 0.3 M) and stirred, and n-BuLi (3.533 mL, 8.834 mmol, 2.1 eq) was added dropwise. HfCl$_4$ (1.415 g, 4.417 mmol, 1.05 eq) was added and the mixture was heated at 90 to 100° C. for 2 hours. After the reaction was complete, the reaction mixture was cooled and MeMgBr (4.907 mL, 14.72 mmol, 3.5 eq, 3.0 M in DEE) was added and allowed to react at room temperature overnight. The solvent was vacuum-dried and filtered. Accordingly, 290 g of the product was obtained in a yield of 10%.

$^1$H-NMR (toluene_d8): 7.63 (d, 1H), 7.26 (d, 2H), 7.15 (m, 4H), 7.10 (m, 2H), 7.07 (m, 4H), 7.03 (m, 3H), 6.67 (t, 2H), 6.02 (s, 1H), 4.84 (m, 1H), 4.13 (m, 1H), 2.990 (m, 1H), 2.60 (m, 2H), 2.18 (m, 1H), 1.82 (m, 1H), (m, 1H), 1.47 (d, 3H), 1.30 (d, 3H), 0.80 (d, 3H), 0.72 (s, 3H), 0.61 (d, 3H), 0.29 (d, 3H), 0.01 (s, 3H)

Example 8: Synthesis of Ligand Compound a) Preparation of N-(t-butyl)-1-(6-bromopyridin-2-yl) Methanimine

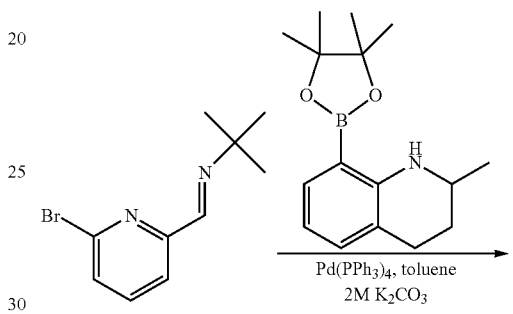

2-formyl-6-bromopyridine (3 g, 16.13 mmol, 1 eq), p-toluenesulfonic acid (3 drops) and a molecular sieve (1 g) were added to a Schlenk flask, and then toluene (32.26 mL, 0.5 M) was added thereto. t-BuNH$_2$ (1.30 g, 17.74 mmol, 1.1 eq) was added thereto, stirred overnight at 70° C., and then cooled to room temperature. After the molecular sieve was filtered, the solvent was vacuum-dried and removed, precipitation was carried out using cold MeOH to produce a solid, and thereby the product was obtained. Accordingly, 3.2 g of a white solid was obtained in a yield of 82.3%.

b) Preparation of N-(t-butyl)-1-(6-(1,2,3,4-tetrahydro-2-methylquinolin-8-yl)pyridin-2-yl) Methanimine

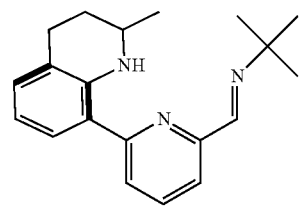

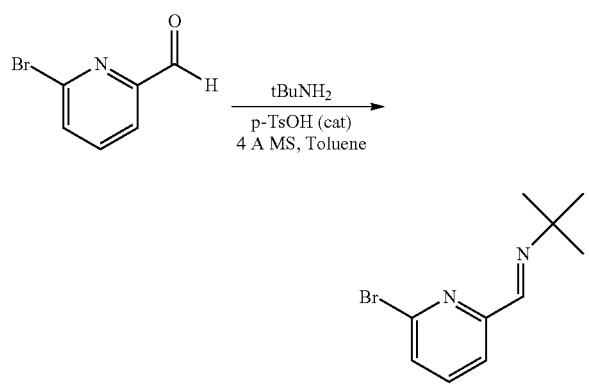

N-(t-butyl)-1-(6-bromopyridin-2-yl) methanimine (3 g, 12.44 mmol, 1 eq) prepared as above was added to toluene (20 mL) and stirred. Meanwhile, separately, Na$_2$CO$_3$ (3.30 g, 31.1 mmol, 2.5 eq) and methyltetrahydroquinoline-borolane (MeTHQ-borolane) (3.4 g, 12.44 mmol, 1 eq) was added to a solution including H$_2$O (4 mL) and EtOH (4 mL) in a ratio of 1:1, and stirred.

The N-(t-butyl)-1-(6-bromopyridin-2-yl) methanimine toluene solution was transferred to the solution of Na$_2$CO$_3$ and THQ-borolane, followed by the addition of Pd(PPh$_3$)$_4$ (0.043 g, 0.0373 mmol, 0.3 mol % Pd). The mixture was stirred at 70° C. overnight and cooled to room temperature. An organic layer was extracted with toluene/brine and dehydrated with Na$_2$SO$_4$. An attempt to produce a solid using EtOH and MeOH was conducted, but the solid was not well formed, and thus the following reaction had to proceed in a state where the starting material was included (a purity of 70%). 4 g of an orange oily product was obtained as the product in a yield of >100%.

c) Preparation of 2-methyl-N-((6-(2-methyl-1,2,3,4-tetrahydro-methylquinolin-8-yl)pyridin-2-yl)(phenyl) methyl) propan-2-amine

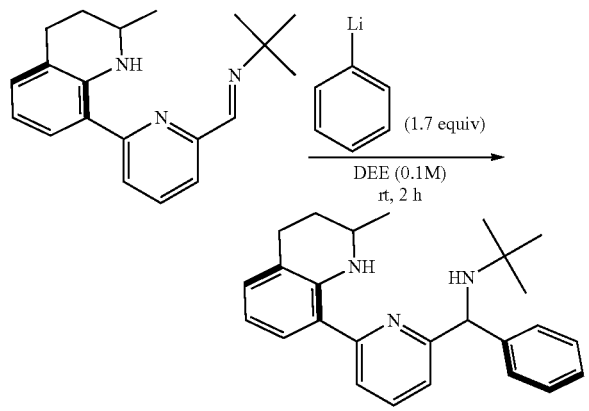

N-(t-butyl)-1-(6-(1,2,3,4-tetrahydro-2-methylquinolin-8-yl)pyridin-2-yl) methanimine (1.17 g, 3.806 mmol, 1 eq) prepared as above was dissolved in diethyl ether (0.1 M), the temperature was lowered to −78° C., phenyl lithium (5.71 mL, 10.275 mmol, 2.7 eq) was added and then the temperature was raised to room temperature. After a reaction was performed overnight, the reaction was checked by TLC and the reaction mixture was quenched with 1 N NH$_4$Cl and worked up with diethyl ether and water. Dehydration was performed using Na$_2$SO$_4$ and the solvent was vacuum-dried with a rotavapor. 1.52 g of orange oil was obtained in a yield of >100%.

$^1$H-NMR (toluene_d8): 8.52 (m, 12H), 5.14 (m, 1H), 3.34-1.38 (m, 6H), 1.05 (s, 3H), 1.01 (s, 9H)

Example 8-1: Synthesis of Transition Metal Compound (Formula 2o)

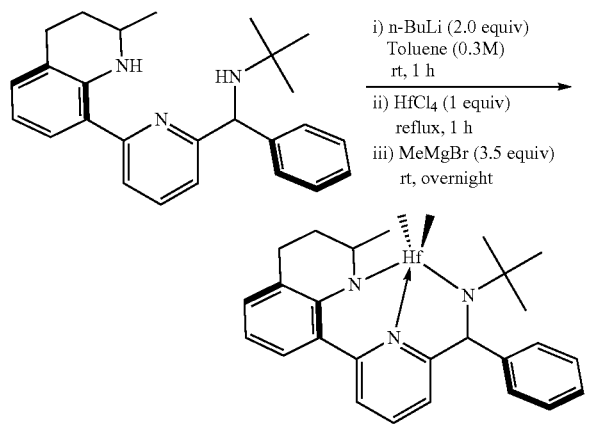

N-((6-(1,2,3,4-tetrahydro-2-methylquinolin-8)pyridin-2-yl)(phenyl) methyl))-t-butan-1-amine (0.86 g, 2.2305 mmol, 1 eq) which was the ligand synthesized in c) of Example 8 was dissolved in toluene (7.435 mL, 0.3 M) and stirred, and n-BuLi (1.874 mL, 4.684 mmol, 2.1 eq) was added dropwise at −40° C. HfCl$_4$ (0.75015 g, 2.342 mmol, 1.05 eq) was added, and the mixture was heated at 90 to 100° C. for 2 hours.

After the reaction was complete, the reaction mixture was cooled to room temperature and MeMgBr (2.602 mL, 7.807 mmol, 3.5 eq, 3.0 M in DEE) was added and allowed to react at room temperature overnight. The solvent was vacuum-dried and then filtered. 210 mg of a brown solid product was obtained in a yield of 16%. NMR showed the presence of the isomer.

$^1$H-NMR (toluene_d8): 7.40-6.60 (m, 11H), 5.84 (m, 1H), 5.00-1.8 (m, 5H), 1.53-0.18 (m, 18H)

Example 9: Synthesis of Ligand Compound

Preparation of N-((2-isopropylphenyl) (6-(2-methyl-1,2,3,4-tetrahydroquinolin-8-yl)pyridin-2-yl)-2-methylpropane-2-amine

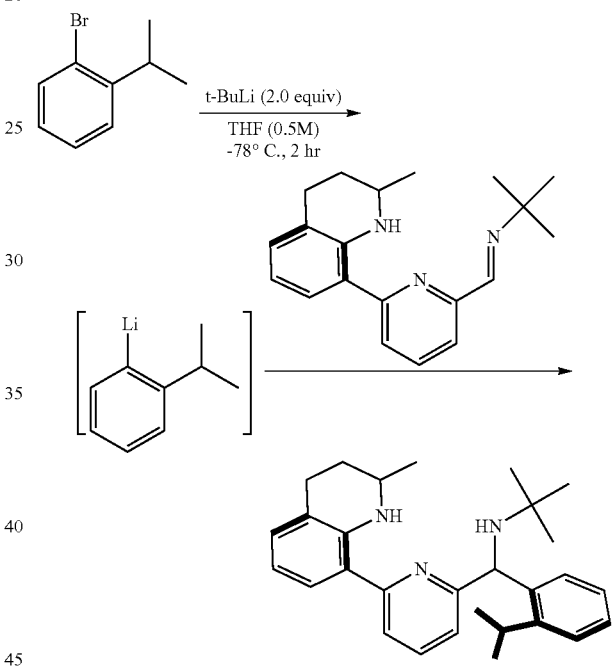

1-Br-2-isopropylbenzene (1.626 g, 8.167 mmol, 2.7 eq) was added to THF (21.38 mL), and t-BuLi (10.404 mL, 16.335 mmol, 5.4 eq) was added at −78° C. The mixture was reacted for 2 hours, and the temperature was raised to room temperature to obtain 1-lithium-2-isopropylbenzene.

N-(t-butyl)-1-(6-(1,2,3,4-tetrahydro-2-methylquinolin-8-yl)pyridin-2-yl) methanimine which was the ligand precursor prepared in Example 17 was dissolved in diethyl ether (30.25 mL, 0.1 M), and 1-lithium-2-isopropylbenzene prepared as above was transferred thereto. After the reaction was allowed to proceed overnight at room temperature, the reaction was checked by TLC. When the reaction was complete, the reaction mixture was quenched with 1 N NH$_4$Cl and an organic layer was worked up with ether/H$_2$O, and dehydrated with Na$_2$SO$_4$. The solvent was vacuum-dried with a rotavapor. 1.14 g of orange oil was obtained in a yield of >100%.

$^1$H-NMR (toluene_d8): 8.28-6.62 (m, 11H), 5.52 (s, 1H), 3.66-1.40 (m, 7H), 1.14 (s, 3H), 1.06 (s, 15H)

Example 9-1: Synthesis of Transition Metal Compound (Formula 2q)

<Synthesis of Transition Metal Compound>

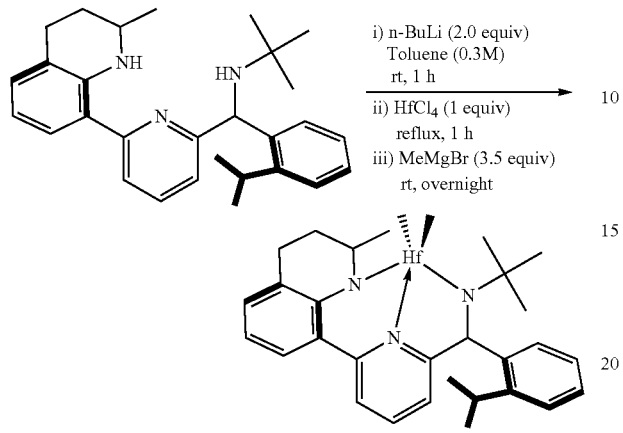

N-((6-(1,2,3,4-tetrahydro-2-methylquinoline-8-yl)pyridin-2-yl)(2-isopropylphenyl)methyl)-t-butan-1-amine (1.23 g, 2.876 mmol, 1 eq) which was the ligand synthesized in Example 9 was dissolved in toluene (9.587 mL, 0.3 M) and stirred, and n-BuLi (2.416 mL, 6.0401 mmol, 2.1 eq) was added dropwise at −40° C. HfCl₄ (0.967 g, 3.0198 mmol, 1.05 eq) was added, and the mixture was heated at 90 to 100° C. for 2 hours.

After the reaction was complete, the reaction mixture was cooled, and MeMgBr (3.355 mL, 10.066 mmol, 3.5 eq, 3.0 M in DEE) was added and allowed to react at room temperature overnight. The solvent was vacuum-dried and then filtered. The obtained product seemed to have several isomers and 588 mg of a brown solid product was obtained in a yield of 32%.

$^1$H-NMR (toluene_d8): 7.38-6.52 (m, 10H), 5.04-2.47 (m, 7H), 1.489-0.88 (m, 24H)

Example 10: Synthesis of Ligand Compound

Preparation of 2,6-diisopropyl-N-((6-(2-methyl-1,2,3,4-tetrahydroquinoline-8-yl)pyridin-2-yl)(naphthyl)methyl) Aniline

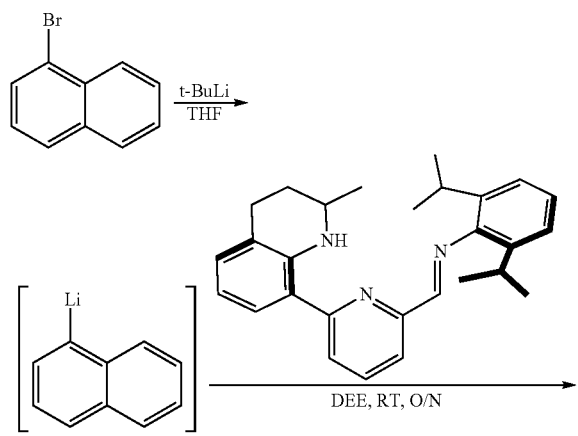

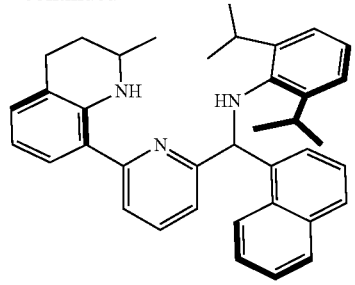

N-(2,6-diisopropylphenyl)-1-(6-(2-methyl-1,2,3,4-tetrahydroquinolin-8-yl)pyridin-2-yl) methanimine (1.5 g, 3.644 mmol, 1 eq) which was the ligand precursor prepared in b) of Example 5 was dissolved in diethyl ether (36.44 mL), and the temperature was lowered to −78° C. After 1-bromonaphthalene (2.04 g, 9.84 mmol, 2.7 eq) was dissolved in THF (19.68 mL), t-BuLi (12.53 mL, 19.68 mmol, 5.4 eq) was added to perform a lithium substitution reaction. When the lithium substitution reaction was complete, the reaction mixture was transferred to the N-(2,6-diisopropylphenyl)-1-(6-(2-methyl-1,2,3,4-tetrahydroquinolin-8-yl)pyridin-2-yl) methanimine solution. When the reaction was complete, the reaction mixture was quenched with 1 N NH₄Cl, and worked up with diethyl ether and water. Accordingly, 1.93 g of yellow oil was obtained as a product in a yield of 98%.

$^1$H-NMR (toluene_d8): 8.401-5.909 (m, 17H), 4.45-1.20 (10H, m), 1.09-0.38 (m, 15H)

Example 10-1: Synthesis of Transition Metal Compound (Formula 2s)

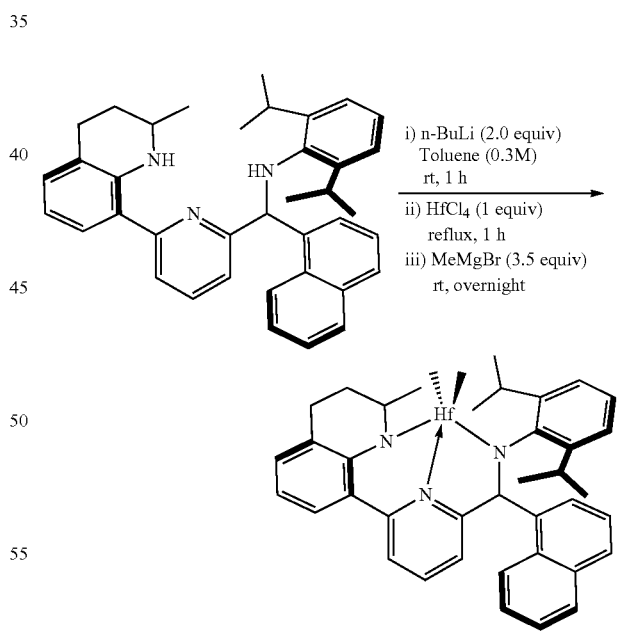

2,6-diisopropyl-N-((6-(2-methyl-1,2,3,4-tetrahydroquinoline-8-yl)pyridin-2-yl)(naphthyl) methyl) aniline (1.13 g, 2.0935 mmol, 1 eq) which was the ligand prepared in Example 10 was added to toluene (6.98 mL, 0.3 M) and stirred, and n-BuLi (1.76 mL, 4.396 mmol, 2.1 eq) was added dropwise. HfCl₄ (0.704 g, 2.198 mmol, 1.05 eq) was added and the mixture was heated for 2 hours at 90 to 100° C.

After the reaction was complete, the reaction mixture was cooled, and MeMgBr (2.44 mL, 7.33 mmol, 3.5 eq, 3.0 M in DEE) was added and allowed to react at room temperature overnight. The solvent was vacuum-dried and then filtered. 210 mg of a yellow solid product was obtained in a yield of 13%.

$^1$H-NMR (toluene_d8): 7.60-6.38 (m, 16H), 4.87 (m, 1H), 3.27-1.81 (m, 7H), 1.30-0.0 (m, 2H)

Example 11: Synthesis of Ligand Compound

Preparation of 2,6-diisopropyl-N-((6-(2-methyl-1,2,3,4-tetrahydroquinoline-8-yl)pyridin-2-yl)(4-tert-butylphenyl)methyl) Aniline

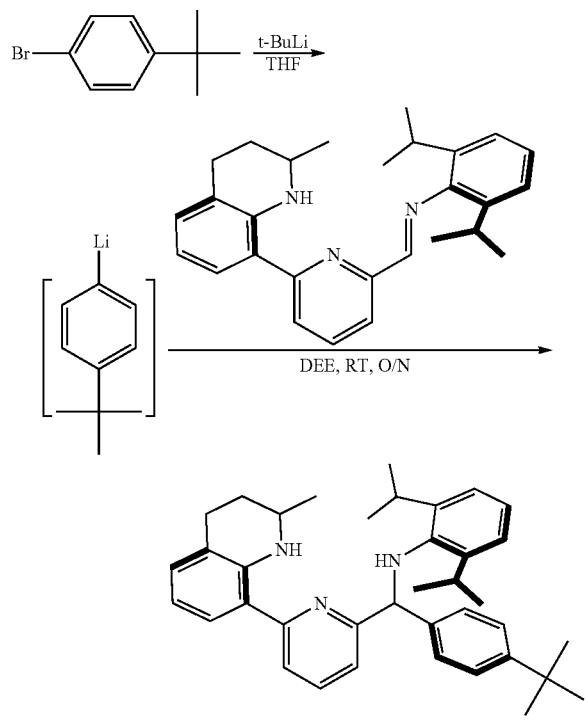

N-(2,6-diisopropylphenyl)-1-(6-(2-methyl-1,2,3,4-tetrahydroquinolin-8-yl)pyridin-2-yl) methanimine (2.146 g, 5.215 mmol, 1 eq) which was the ligand precursor prepared in b) of Example 5 was dissolved in diethyl ether (52.15 mL), and the temperature was lowered to −78° C. After 1-tert-butyl-4-bromophenyl (3 g, 14.08 mmol, 2.7 eq) was dissolved in THF (28.16 mL), t-BuLi (17.82 mL, 28.161 mmol, 5.4 eq) was added to perform a lithium substitution reaction. When the lithium substitution reaction was complete, the reaction mixture was transferred to the N-(2,6-diisopropylphenyl)-1-(6-(2-methyl-1,2,3,4-tetrahydroquinolin-8-yl)pyridin-2-yl) methanimine solution. When the reaction was complete, the reaction mixture was quenched with 1 N NH$_4$Cl, and worked up with diethyl ether and water. Accordingly, 2.0 g of orange solid was obtained as the product in a yield of 70%.

$^1$H-NMR (toluene_d8): 8.23-6.64 (m, 14H), 5.33-1.50 (m, 9H), 1.21-0.99 (m, 24H)

Example 11-1: Synthesis of Transition Metal Compound (Formula 2u)

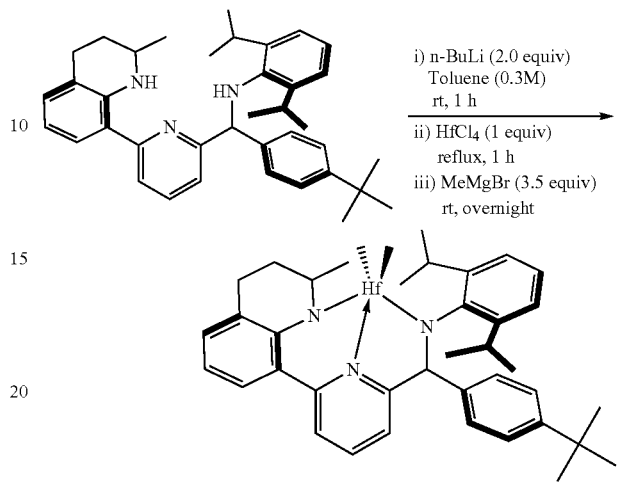

2,6-diisopropyl-N-((6-(2-methyl-1,2,3,4-tetrahydroquinoline-8-yl)pyridin-2-yl)(4-tert-butylphenyl)methyl)aniline (1 g, 1.832 mmol, 1 eq) which was the ligand prepared in Example 11 was added to toluene (6.107 mL, 0.3 M) and stirred, and n-BuLi (1.539 mL, 3.847 mmol, 2.1 eq) was added dropwise. HfCl$_4$ (0.616 g, 1.9236 mmol, 1.05 eq) was added thereto, and the mixture was heated at 90 to 100° C. for 2 hours.

After the reaction was complete, the reaction mixture was cooled, and MeMgBr (2.137 mL, 6.412 mmol, 3.5 eq, 3.0 M in DEE) was added and allowed to react at room temperature overnight. The solvent was vacuum-dried and then filtered. 1.04 g of a red solid product was obtained in a yield of 75%.

$^1$H-NMR (toluene_d8): 7.32-5.93 (m, 13H), 4.81-1.80 (m, 8H), 1.15-0.00 (m, 30H)

Example 1-A: Preparation of Ethylene-Octene Copolymer

A hexane solvent (1.0 L), octene (280 mL) and ethylene (35 bar) were added to a 2 L autoclave reactor, a pressure was set as 500 psi using high argon pressure, and the temperature of the reactor was pre-heated to 120° C. 10 equivalents of a 5×10$^{-6}$ M dimethylanilinium tetrakis(pentafluorophenyl)borate cocatalyst was added in the reactor while applying high argon pressure, and the transition metal compound (1×10$^{-6}$ M, 2.0 mL) of Example 1-1 treated with a triisobutyl aluminum compound was placed in a catalyst storage tank and added in the reactor while applying high argon pressure. The polymerization reaction was performed for 10 minutes. The reaction heat was removed through a cooling coil inside the reactor to maintain the polymerization temperature as constant as possible. After the polymerization reaction proceeded for 10 minutes, a residual gas was exhausted, and a polymer solution was discharged to the lower part of the reactor, and an excessive amount of ethanol was added thereto to induce precipitation. The obtained polymer was washed with ethanol and acetone twice and three times, respectively, and was dried in a vacuum oven at 90° C. for at least 12 hours to prepare an ethylene-octene copolymer.

Example 1-B, 2-A to 11-A: Preparation of Ethylene-Octene Copolymer

An ethylene-octene copolymer was prepared in the same manner as in Example 1-A except that each transition metal compound as shown in the following Table 6 was treated with a triisobutyl aluminum compound and used instead of the transition metal compound of Example 1-1 treated with the triisobutyl aluminum compound in Example 1-A.

Experimental Example 1: Measurement of Catalytic Activity

The catalyst activity in the preparation of the copolymers in Examples 1-A to 7-A, 10-A and 11-A was measured by the following method, and the results are shown in Table 6 below.

The catalytic activity was calculated using the molar ratio of the transition metal compound to the total yield of the prepared copolymer. Specifically, the ratio of a value obtained by measuring the mass of a part of the reaction solution taken after completion of the polymerization reaction to a value obtained by heating a part of the copolymer at 120° C. for 10 minutes to remove both the hexane solvent and the residual monomer and measuring the mass of the remaining copolymer was calculated. Based on this, the catalytic activity was calculated using the mass of the resulting copolymer, the number of moles of the transition metal compound used in the polymerization reaction, and the polymerization time.

TABLE 6

| | Transition metal compound | Catalytic activity (KgPE/mmol) |
|---|---|---|
| Example 1-A | Example 1-1 | 2.7 |
| Example 1-B | Example 1-2 | 0.8 |
| Example 2-A | Example 2-1 | 5.6 |
| Example 2-B | Example 2-2 | 0.74 |
| Example 3-A | Example 3-1 | 1.0 |
| Example 4-A | Example 4-1 | 2.2 |
| Example 5-A | Example 5-1 | 2.3 |
| Example 6-A | Example 6-1 | 5.3 |
| Example 7-A | Example 7-1 | 2.7 |
| Example 10-A | Example 10-1 | 2.3 |
| Example 11-A | Example 11-1 | 1.5 |

As can be seen in Table 6, the transition metal compounds of Examples 1-1 to 7-1, 10-1, and 11-1 exhibited catalytic activity in the preparation of the ethylene-octene copolymer.

Experimental Example 2: Measurement of Physical Properties

The melt index (MI), density, and melting point of the polymers prepared in Examples 6-A, 7-A and 10A were measured by the following methods, and the results are shown in Table 7 below.

(1) The melt index (MI) of the polymer was measured by ASTM D-1238 (condition E, 190° C., a load of 2.16 kg).

(2) The density of the polymer was measured by ASTM D-792.

(3) The melting point (Tm) was measured using Q100 manufactured by TA Co.

TABLE 7

| | Transition metal compound | Catalytic activity (KgPE/mmol) | MT (g/10 min) | Density (g/cc) | Melting point (° C.) |
|---|---|---|---|---|---|
| Example 6-A | Example 6-1 | 5.3 | 0.02 | 0.865 | 50.3 |
| Example 7-A | Example 7-1 | 2.7 | 0.02 | 0.883 | 72.9 |
| Example 10-A | Example 10-1 | 2.3 | 0.01 | 0.873 | 60.9 |

As can be seen Table 7, polymers of Examples 6-A, 7-A and 10A prepared using the transition metal compound of Examples 6-1, 7-1, and 10-1 which are examples of the transition metal compound of the present invention showed a low melt index (MI) of 0.02 or less, which indicates a high molecular weight, and a density of 0.883 g/cc or less. Particularly, polymers of Examples 6-A and 10-A prepared using the transition metal compounds of Examples 6-1 and 10-1 showed a low density of 0.873 g/cc or less and a low melt index (MI) of 0.02 or less, which indicate a low density and a high molecular weight.

The invention claimed is:

1. A ligand compound represented by the following Formula 1:

[Formula 1]

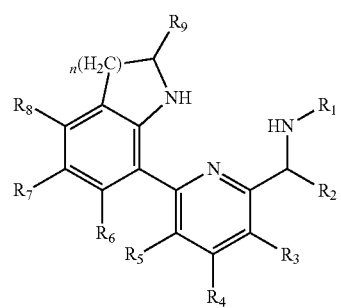

in Formula 1, $R_1$ to $R_9$ each independently represent hydrogen, a silyl, an alkyl having 1 to 20 carbon atoms, an alkenyl having 2 to 20 carbon atoms, an aryl having 6 to 20 carbon atoms, an alkylaryl having 7 to 20 carbon atoms, an arylalkyl having 7 to 20 carbon atoms or a metalloid radical of a Group 14 metal substituted with a hydrocarbyl having 1 to 20 carbon atoms; two or more adjacent groups of the $R_1$ to $R_8$ are optionally connected to each other to form an aliphatic ring having 5 to 20 carbon atoms or an aromatic ring having 6 to 20 carbon atoms; the aliphatic ring or aromatic ring is optionally substituted with a halogen, an alkyl having 1 to 20 carbon atoms, an alkenyl having 2 to 20 carbon atoms or an aryl having 6 to 20 carbon atoms; and n is 1 or 2.

2. The ligand compound according to claim 1, wherein, in Formula 1, $R_1$ to $R_9$ each independently represent hydrogen, an alkyl having 1 to 20 carbon atoms, an aryl having 6 to 20 carbon atoms, an alkylaryl having 7 to 20 carbon atoms, or an arylalkyl having 7 to 20 carbon atoms; two or more adjacent groups of the $R_1$ to $R_8$ are optionally connected to each other to form an aliphatic ring having 5 to 20 carbon atoms or an aromatic ring having 6 to 20 carbon atoms; and the aliphatic ring or aromatic ring is optionally substituted with a halogen, an alkyl having 1 to 20 carbon atoms, or an aryl having 6 to 20 carbon atoms.

3. The ligand compound according to claim 1, wherein the compound of Formula 1 is one of the following compounds:
[Formula 1a]
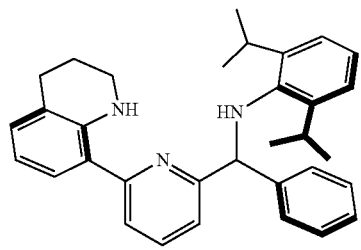
[Formula 1b]
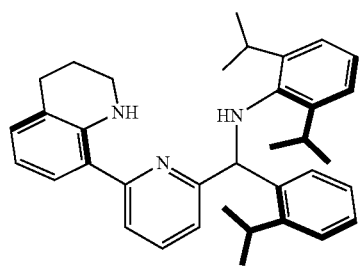
[Formula 1c]
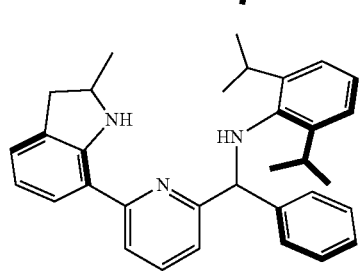
[Formula 1d]
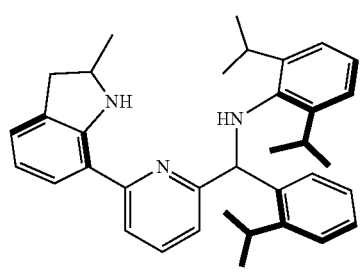
[Formula 1e]
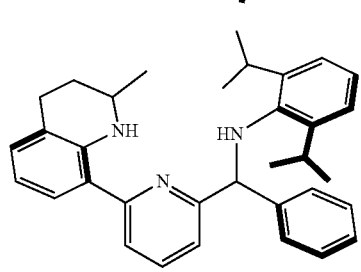
[Formula 1f]
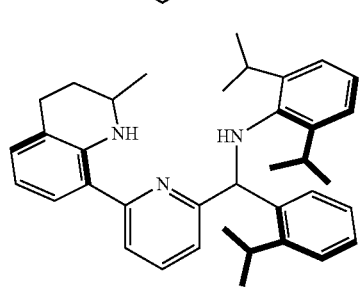
-continued
[Formula 1g]
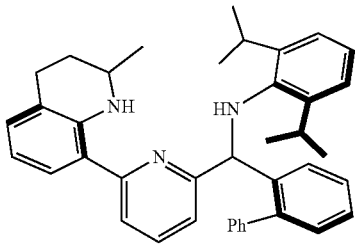
[Formula 1h]
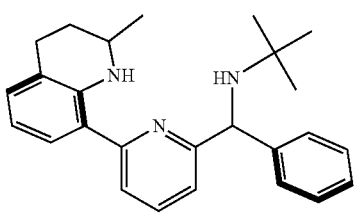
[Formula 1i]
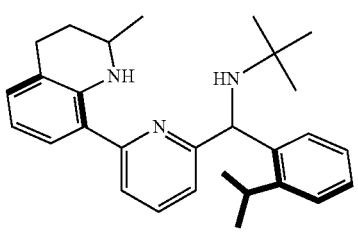
[Formula 1j]
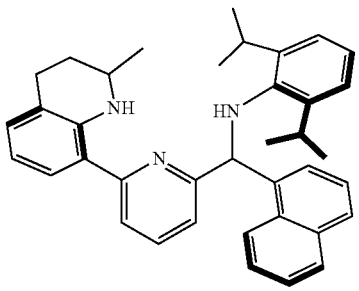
[Formula 1k]
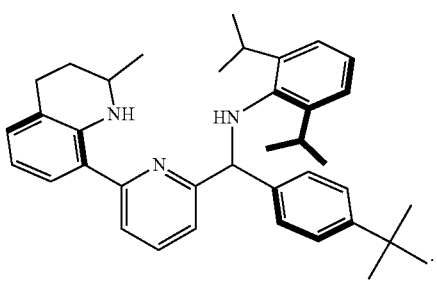
* * * * *